(12) United States Patent
Woods et al.

(10) Patent No.: US 9,169,498 B2
(45) Date of Patent: Oct. 27, 2015

(54) RECOVERY OF DESIRED CO-PRODUCTS FROM FERMENTATION STILLAGE STREAMS

(71) Applicant: Primafuel, Inc., Long Beach, CA (US)

(72) Inventors: Richard Root Woods, Three Rivers, CA (US); Vahik Krikorian, La Canada, CA (US); Juston Smithers, Albany, CA (US)

(73) Assignee: Edeniq, Inc., Visalia, CA (US)

( * ) Notice: Subject to any disclaimer, the term of this patent is extended or adjusted under 35 U.S.C. 154(b) by 0 days.

(21) Appl. No.: 14/071,404

(22) Filed: Nov. 4, 2013

(65) Prior Publication Data

US 2014/0220650 A1    Aug. 7, 2014

Related U.S. Application Data

(63) Continuation of application No. 13/546,548, filed on Jul. 11, 2012, now Pat. No. 8,609,874, which is a continuation of application No. 13/164,088, filed on Jun. 20, 2011, now Pat. No. 8,236,977, which is a continuation of application No. PCT/US2010/033491, filed on May 4, 2010.

(60) Provisional application No. 61/175,423, filed on May 4, 2009, provisional application No. 61/175,424, filed on May 4, 2009.

(51) Int. Cl.
*C12P 7/10* (2006.01)
*C11B 1/10* (2006.01)
*C11B 13/00* (2006.01)

(52) U.S. Cl.
CPC ... *C12P 7/10* (2013.01); *C11B 1/10* (2013.01); *C11B 13/00* (2013.01); *Y02E 50/16* (2013.01); *Y02W 30/74* (2015.05)

(58) Field of Classification Search
None
See application file for complete search history.

(56) References Cited

U.S. PATENT DOCUMENTS

| | | | |
|---|---|---|---|
| 2,216,904 A | 10/1940 | Brown | |
| 2,216,905 A | 10/1940 | Brown et al. | |
| 2,239,747 A | 4/1941 | Thurman | |
| 2,263,608 A | 11/1941 | Brown | |
| 2,437,036 A * | 3/1948 | Murer et al. | 127/67 |
| 2,615,029 A | 10/1952 | Rosten | |
| 2,663,718 A | 12/1953 | Strezynski | |
| 3,440,253 A | 4/1969 | Koebner et al. | |
| 4,341,713 A * | 7/1982 | Stolp et al. | 554/17 |
| 4,812,225 A | 3/1989 | Corti et al. | |
| 5,177,008 A * | 1/1993 | Kampen | 435/139 |
| 5,223,601 A | 6/1993 | Chum et al. | |
| 5,316,782 A | 5/1994 | Zimlich | |
| 5,662,179 A | 9/1997 | Falk | |
| 7,601,858 B2 | 10/2009 | Cantrell et al. | |
| 7,858,140 B2 * | 12/2010 | Paustian et al. | 426/622 |

(Continued)

OTHER PUBLICATIONS

Hagenmaier, R. et al., Aqueous processing of resh coconuts for recovery of oil and coconut skim milk, 1973, Journal of Food Science, vol. 38, pp. 516-518.

(Continued)

*Primary Examiner* — Yate K Cutliff
(74) *Attorney, Agent, or Firm* — Kilpatrick Townsend & Stockton LLP

(57) ABSTRACT

Processes and methods of recovering desired products from fermentation stillage are presented, including processes and methods of recovering lipids and aqueous materials.

19 Claims, 16 Drawing Sheets

(56) References Cited

U.S. PATENT DOCUMENTS

| | | |
|---|---|---|
| 2004/0087808 A1 | 5/2004 | Prevost et al. |
| 2006/0037104 A1 | 2/2006 | Green et al. |
| 2006/0041152 A1 | 2/2006 | Cantrell et al. |
| 2006/0099693 A1 | 5/2006 | Kobzeff et al. |
| 2006/0286649 A1 | 12/2006 | Bailey et al. |
| 2008/0105282 A1 | 5/2008 | Fernholz et al. |
| 2008/0110577 A1 | 5/2008 | Winsness |
| 2009/0064567 A1 | 3/2009 | Lippmeier et al. |
| 2009/0181436 A1 | 7/2009 | Beecher et al. |

OTHER PUBLICATIONS

Minowa, T. et al.; "Oil production from buckwheat stillage by thermochemical liquefaction"; 1993, *Jounal of NIRE*, vol. 2, No. 4, pp. 53-62, abstract from NTIS.

Winfield, H., The oil of maize, 1899, The Chemical Publishing company (56 pages, including Google cover sheet).

Yukata, Y. et al.; "Liquefaction of barley stillage and upgrading of primary oil"; 1991, *Biomass and Bioenergy*, vol. 1, No. 6, pp. 305-370, abstract from Dechema.

\* cited by examiner

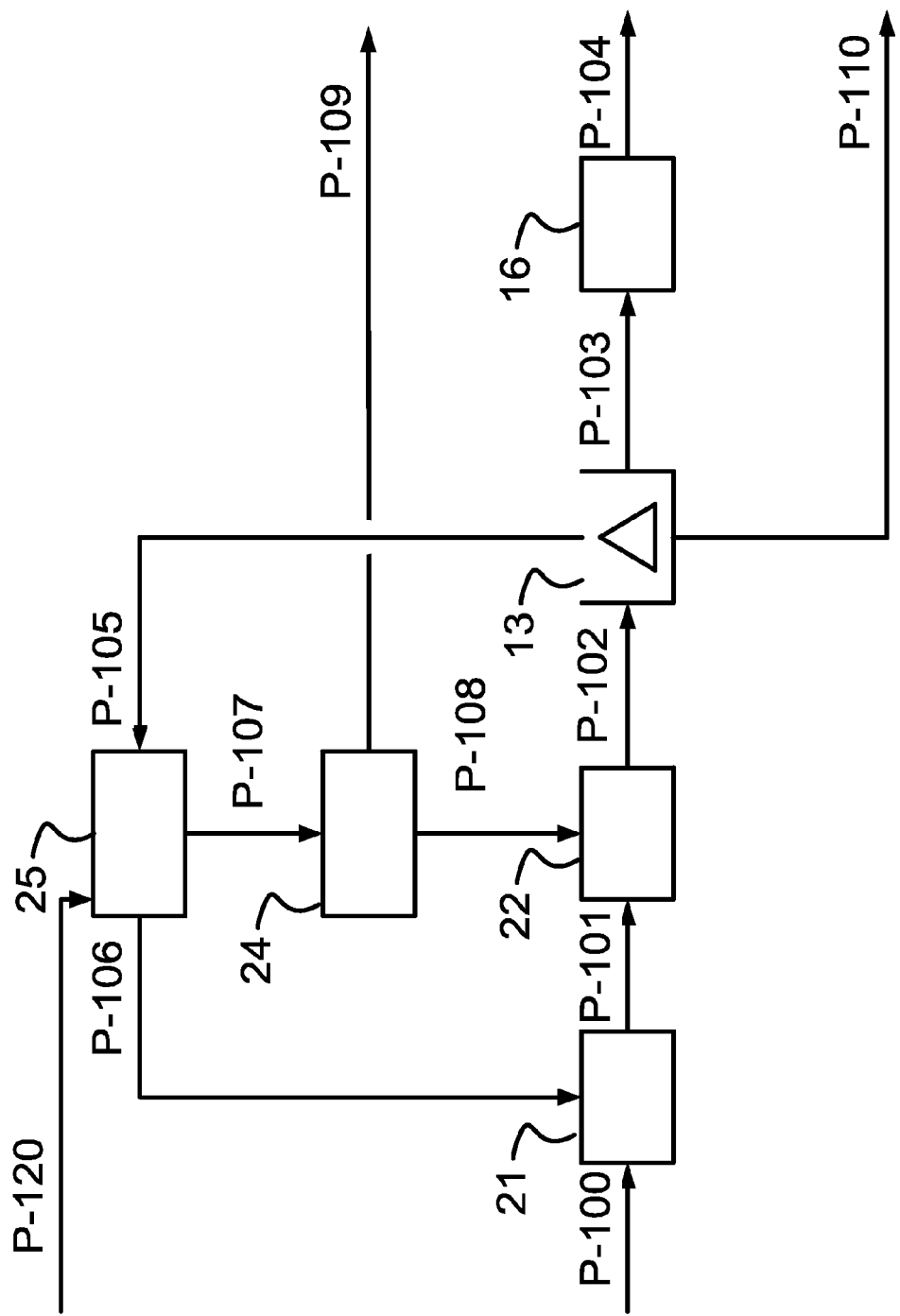

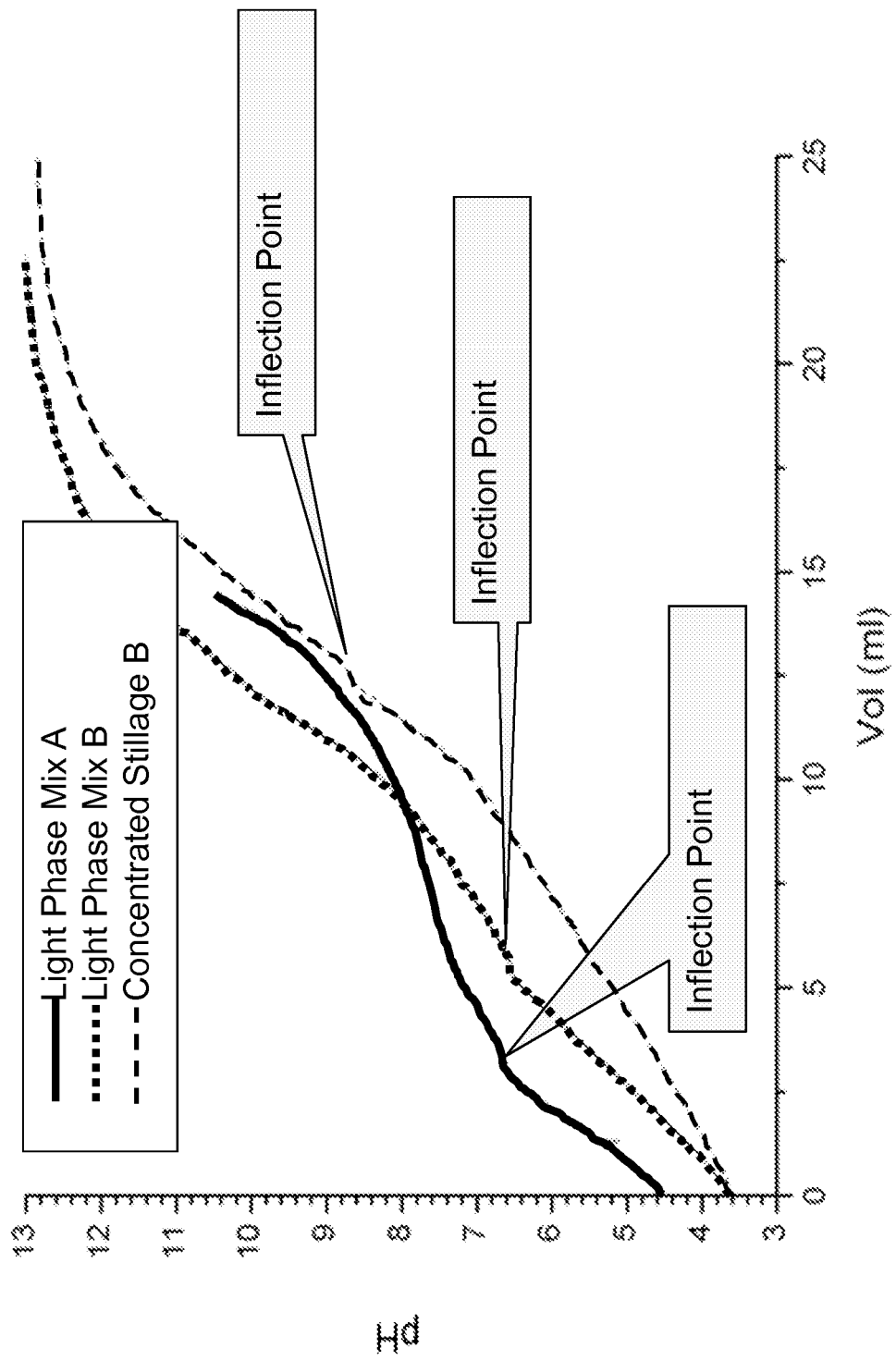
FIG 7. Superimposed titration curves for Concentrated Stillage, Light Phase Mixture A and Light Phase Mixture B showing the dependence of pH on the volumetric addition of 5wt% caustic solution

|  | Top Layer | Second Layer | Third Layer | Fourth Layer |
|---|---|---|---|---|
| 201 Concentrated Stillage | Only one layer Light yellow color 100% of sample | 0% of sample | 0% of sample | 0% of sample |
| 202 Concentrated Stillage after Centrifuge | Trace free oil Less than 1% of Sample | Fluffy Emulsion Light yellow color 17% of sample | Aqueous phase Light tan color 63% of sample | Simi-solid phase Light Tan color 20% of sample |
| 203 Light Phase Mixture | Fluffy emulsion Light yellow color 100% of sample | 0% of sample | 0% of sample | 0% of sample |
| 204 pH Treated Light Phase Mixture | Emulsion Light tan color 100% of sample | 0% of sample | 0% of sample | 0% of sample |
| 205 pH Treated Light Phase Mixture after Centrifuge | Free Oil Clear red color 28% of sample | Emulsion Light tan color 5% of sample | Aqueous phase Clear brown color 30% of sample | Simi-solid phase Tan color 38% of sample |

FIG 8

RECOVERY OF DESIRED CO-PRODUCTS FROM FERMENTATION STILLAGE STREAMS

CROSS-REFERENCES TO RELATED APPLICATIONS

This application is a continuation of U.S. patent application Ser. No. 13/546,548, filed Jul. 11, 2012, which is a continuation of U.S. patent application Ser. No. 13/164,088, filed Jun. 20, 2011, now U.S. Pat. No. 8,236,977, which is a continuation of PCT/US2010/033491, filed May 4, 2010, which claims the benefit under 35 U.S.C. §1.119(e) of U.S. Application Nos. 61/175,423 and 61/175,424, both filed May 4, 2009, each of which is incorporated by reference in their entirety for all purposes.

BACKGROUND OF THE INVENTION

1. Field of the Invention

The present invention refers to methods of enhancing the recovery of desired co-products from post fermentation stillage streams and to processes that recover lipid-rich fractions and aqueous fractions rich in organic acids, glycerin and other compounds present in or derivable from the post fermentation broth.

2. Description of the Related Art

Ethanol production using a wide variety of feedstocks has emerged as an alternative for the replacement of fuels such as gasoline in the transportation and other markets. Feedstocks can include starch-containing agricultural products such as corn, wheat and sorghum sugar-based agricultural products derived from sugar cane, sugar beets, etc.; emerging cellulosic- and lignocellulosic-based biomass from agricultural wastes such as corn stover, rice hulls, and lumber operations, and purpose grown plants and organisms such as switchgrass, Panicum virgatum, Miscanthus, trees, brush, algae, and the like.

For starch based ethanol production, the two most common processes in the United States—the dry-grind process and the wet-mill process. Dry-grind facilities represent the majority of the existing corn ethanol plants in the United States and most of which can generally be described as utilizing a process in which 100% of the corn's composition is fed to the fermentation process. Dry-grind facilities have the advantages of lower overall capital cost, 100% of the fermentable feed enters the fermentation reactors, and free lipids from the feed in the fermentation liquids functions as an anti-foaming agent. Corn oil can be removed in a dry-grind facility by several methods including up-front fractionation of the incoming ground corn, mechanical separation from various stillage streams, and solvent extraction from dried byproducts.

In wet-mill facilities the corn is preprocessed and fractionated into different components such as the germs, glutens, and fibers prior to the fermentation process. The germ contains the majority of the corn oil contained in the kernel. The corn oil can be obtained by mechanical extrusion of the germ, and/or by solvent extraction. The advantages of the wet-mill process is that additional by-products can be extracted prior to the fermentation process, but the disadvantages are much higher overall capital cost, less than 100% of the fermentable feed enters the fermentation reactors resulting in lower ethanol production per mass of feed, and increased operating costs for anti-foaming agents.

Realization that the fermentation by-product streams have potential value is well known in the industry. As early as the 1940s, Brown in U.S. Pat. No. 2,211,604, U.S. Pat. No. 2,221,605, and U.S. Pat. No. 2,263,608 referenced the extraction of animal feed and oil extraction and taught autoclaving of stillage streams to enhance filtration and support downstream solvent extraction. In 1953, Strezynski in U.S. Pat. No. 2,663,718 taught the recovery of oil from distillery stillage using a tri-phase separation centrifuge. This art was again discussed by Prevost in publication US2004/0087808 A1 and Cantrell in publication US 2006/0041152 A1, both of which disclose the recovery of a corn oil co-product from stillage streams of dry grind ethanol facilities using centrifuges. As early as 1911 von Laszloffy disclosed in U.S. Pat. No. 1,147,767 and U.S. Pat. No. 1,147,768 the presence of desirable compounds in waste distillers slop or stillage. In 1993 Kampen, in U.S. Pat. No. 5,177,008 and in its parent applications U.S. Appl. Ser. No. 381,179, filed Jul. 18, 1989, and U.S. Appl. Ser. No. 136,415, filed Dec. 22, 1987, disclosed a process for the recovery of other desirable compounds including glycerol, succinic acid, lactic acid, and betaine.

With the evolution of the ethanol industry in the United States centrifuges are frequently included in the process to recover crude corn oil from the stillage streams as an additional co-product that can be used for higher value animal feed or feed stock for biodiesel or renewable diesel production. Frequently, these facilities recover a small fraction of the available oil, or recover a low quality product which contains an excessive quantity of solids that must be removed downstream with a series of high cost bulk storage tanks functioning as high volume settling tanks or decanters.

BRIEF SUMMARY OF THE INVENTION

Systems and methods for recovering oil and other materials from stillage are desirable. According to the present invention, any stillage can be used. In some embodiment, the stillage is generated from pretreated biomass particles having a relatively uniform particle size of less than 1600 microns. For example, at least 95% of the pretreated biomass particles have a particle size from about 100 microns to about 800 microns, or a particle size from about 100 microns to about 500 microns. The pretreated biomass particles can be generated by, for example, a hammer mill or a colloid mill.

Accordingly, in a first aspect, a method is provided for recovering oil from stillage, the method comprising in sequence: mechanically separating a light phase oil material stream from the stillage; evaporating water from the light phase oil material to generate a concentrated light phase oil material; and recovering oil from the concentrated light phase oil material.

In some embodiments, at least 10% weight of the stillage is the light phase oil material or as otherwise described herein.

In an embodiment of the first aspect, the stillage is concentrated thin stillage.

In an embodiment of the first aspect, the light phase oil material has a moisture content of greater than about 5% (wt.).

In an embodiment of the first aspect, mechanically separating the light phase oil material comprises centrifugation.

In an embodiment of the first aspect, mechanically separating the light phase oil material comprises centrifugation, and the centrifugation comprises use of a disk type centrifuge.

In an embodiment of the first aspect, mechanically separating the light phase oil material comprises centrifugation, and separating the light phase oil material from the stillage further comprises, generating an aqueous phase mixture and a solids phase mixture in addition to the light phase oil material.

In an embodiment of the first aspect, evaporating water from the light phase oil material comprises heating the light phase oil material.

In an embodiment of the first aspect, evaporating water from the light phase oil material comprises heating the light phase oil material and reducing the pressure of the light phase oil material.

In an embodiment of the first aspect, evaporating water from the light phase oil material comprises heating the light phase oil material, and the evaporating step is preformed on the light phase oil material at a temperature of between about 180° F. and about 280° F.

In an embodiment of the first aspect, the recovering oil step comprises mechanical processing.

In an embodiment of the first aspect, the recovering oil step comprises mechanical processing and the mechanical processing for recovery of oil includes one or more of gravity separation, filtration, centrifugation, or decanting.

In an embodiment of the first aspect, evaporating water from the light phase oil material comprises heating the light phase oil material and reducing the pressure of the light phase oil material, and the evaporating step is performed on the light phase oil material at a pressure of less than 1 atmosphere absolute.

In an embodiment of the first aspect, the separating step is performed on the stillage at a temperature of between about 140° F. and about 212° F.

In an embodiment of the first aspect, the light phase oil material has a moisture content of less than about 50% and greater than about 5% by weight.

In an embodiment of the first aspect, the light phase oil material has a moisture content of less than about 30% and greater than about 5% by weight.

In an embodiment of the first aspect, the stillage is concentrated thin stillage, and the concentrated stillage has a moisture content of less than about 85% and greater than about 50% by weight.

In a second aspect, a method of producing oil is provided, the method comprising: mechanically processing an evaporated light phase oil material, wherein the evaporated light phase oil material was made by evaporating water from a light phase oil material mechanically separated from concentrated thin stillage.

In some embodiments, at least 10% weight of the stillage is the light phase oil material or as otherwise described herein.

In a third aspect, a method of recovering oil from stillage is provided, the method comprising in sequence: mechanically separating a light phase oil material stream from the stillage, where in the light phase oil material stream has a moisture content of greater than about 5%; chemically processing the light phase oil material to generate a pH adjusted mixture with a pH of greater than about 6 and less than about 11; and recovering oil from the pH adjusted mixture.

In some embodiments, at least 10% weight of the stillage is the light phase oil material or as otherwise described herein.

In an embodiment of the third aspect, the stillage is concentrated thin stillage.

In an embodiment of the third aspect, mechanically separating the light phase oil material comprises centrifugation.

In an embodiment of the third aspect, mechanically separating the light phase oil material comprises centrifugation, and the centrifugation comprises use of a disk type centrifuge.

In an embodiment of the third aspect, mechanically separating the light phase oil material comprises centrifugation, and generating an aqueous phase mixture and a solids phase mixture in addition to the light phase oil material.

In an embodiment of the third aspect, chemical processing the light phase oil material comprises the addition of alkali metal or basic, ionic salt.

In an embodiment of the third aspect, chemical processing the light phase oil material comprises the addition of alkali metal or basic, ionic salt, and the alkali metal or basic, ionic salt comprises hydroxide or carbonate ion in a solution.

In an embodiment of the third aspect, chemical processing the light phase oil material comprises the addition of alkali metal or basic, ionic salt, and the basic, ionic salt comprises a solution of sodium hydroxide wherein the concentration of the sodium hydroxide solution is between about 1% and about 99% sodium hydroxide by weight.

In an embodiment of the third aspect, chemical processing the light phase oil material comprises the addition of alkali metal or basic, ionic salt, and the alkali metal or basic, ionic salt comprises hydroxide or carbonate ion in a solution, wherein the solution is between about 5% and about 50% concentration by weight.

In an embodiment of the third aspect, chemical processing the light phase oil material comprises the addition of alkali metal or basic, ionic salt, and the alkali metal or basic, ionic salt comprises hydroxide or carbonate ion in a solution, wherein the solution comprises a clean in place (CIP) solution or a waste CIP solutions.

In an embodiment of the third aspect, the separating step is performed on the concentrated stillage at a temperature of between about 140° F. and about 212° F.

In an embodiment of the third aspect, the chemical processing step is preformed on the light phase oil material at a temperature of between about 100° F. and about 212° F.

In a fourth aspect, a method of recovering oil from stillage is provided, the method comprising in sequence: evaporating and mechanically processing the stillage to create a light phase oil material having a moisture content of greater than about 5% by weight; recovering oil from the light phase oil material by chemically processing the light phase oil material, wherein the chemical processing comprises adjusting the pH of the light phase oil material, and mechanically processing the chemically processed light phase oil material to recovery oil.

In some embodiments, at least 10% weight of the stillage is the light phase oil material or as otherwise described herein.

In an embodiment of the fourth aspect, the step of mechanically processing the stillage comprises using a disk stack centrifuge.

In an embodiment of the fourth aspect, the step of chemically processing the light phase oil material comprises mixing the light phase oil material with alkali metal or basic, ionic salt.

In an embodiment of the fourth aspect, the pH adjustment of the light phase oil material includes adjusting the pH of the light phase oil material to a range of about 6 to about 11.

In an embodiment of the fourth aspect, the pH adjustment of the light phase oil material includes adjusting the pH of the light phase oil material to a range of about 6 to about 10.

In an embodiment of the fourth aspect, the pH adjustment of the light phase oil material includes adjusting the pH of the light phase oil material to a range of about 6 to about 9.

In an embodiment of the fourth aspect, the pH adjustment of the light phase oil material includes adjusting the pH of the light phase oil material to a range of about 6 to about 8.

In an embodiment of the fourth aspect, the pH adjustment of the light phase oil material includes adjusting the pH of the light phase oil material to a range of about 7 to about 9.

In an embodiment of the fourth aspect, the pH adjustment of the light phase oil material includes adjusting the pH of the light phase oil material to within 1.5 pH unit of a pH that corresponds to a pH that would be an inflection point, discontinuity, or change in slope on a titration curve for the concentrated thin stillage being adjusted.

In an embodiment of the fourth aspect, the pH adjustment of the light phase oil material includes adjusting the pH of the light phase oil material to within 1 pH unit of a pH that corresponds to a pH that would be an inflection point, discontinuity, or change in slope on a titration curve for the concentrated thin stillage being adjusted.

In an embodiment of the fourth aspect, the pH adjustment of the light phase oil material includes adjusting the pH of the light phase oil material to within 0.5 pH unit of a pH that corresponds to a pH that would be an inflection point, discontinuity, or change in slope on a titration curve for the concentrated thin stillage being adjusted.

In an embodiment of the fourth aspect, the step of chemically processing the light phase oil material comprises mixing the light phase oil material with alkali metal or basic, ionic salt, and the basic, ionic salt comprises a hydroxide or carbonate ion solution between 5% and 50% by weight salt.

In a fifth aspect, a method of recovering oil from stillage is provided, the method comprising in sequence: heating and evaporating the stillage to create a low volume concentrate with a moisture content of less than about 85% and greater than about 50% by weight; and recovering oil by chemically and mechanically processing the low volume concentrate.

In some embodiments, at least 10% weight of the stillage is the light phase oil material or as otherwise described herein.

In an embodiment of the fifth aspect, the chemical processing of the low volume concentrate comprises mixing basic, ionic salt solution into at least a portion of the low volume concentrate to create a pH adjusted portion of the low volume concentrate with a pH of greater than about 6 and less than about 11.

In an embodiment of the fifth aspect, the chemical processing of the low volume concentrate comprises mixing basic, ionic salt solution into at least a portion of the low volume concentrate to create a pH adjusted portion of the low volume concentrate with a pH of greater than about 6 and less than about 11, wherein the oil is recovered from the pH adjusted portion using mechanical processing.

In an embodiment of the fifth aspect, the mechanical processing comprises separating a portion of the low volume concentrate as a light phase oil material using a centrifuge.

In a sixth aspect, a method of processing whole stillage is provided, the method comprising: recovering thin stillage from whole stillage, the thin stillage including oil and solids; heating and mechanically processing the thin stillage to produce a low volume concentrate portion of the thin stillage with a moisture content greater than about 5% and less than about 50% by weight; chemically processing the low volume concentrate to produce a pH adjusted low volume concentrate with pH greater than about 6 and less than about 11; and recovering oil from the pH adjusted low volume concentrate by a mechanical separation.

In some embodiments, at least 10% weight of the stillage is the light phase oil material or as otherwise described herein.

In a seventh aspect, a method of producing oil is provided, the method comprising: mechanically processing a pH adjusted light phase oil material, wherein the pH adjusted light phase oil material was made by adjusting the pH of a light phase oil material mechanically separated from concentrated thin stillage.

In some embodiments, at least 10% weight of the stillage is the light phase oil material or as otherwise described herein.

In an eighth aspect, a method of recovering compounds from stillage, the method comprising, in sequence: mechanically separating a light phase oil material stream and an aqueous phase mixture stream from stillage, wherein the light phase oil material stream has a moisture content of greater than 5% by weight and a fat concentration of greater than about 50% by weight on a dry mass basis; mechanically processing the aqueous phase mixture to generate a clarified aqueous phase mixture; and recovering compounds from the clarified aqueous phase mixture.

In some embodiments, at least 10% weight of the stillage is the light phase oil material or as otherwise described herein.

In an embodiment of the eighth aspect, the mechanical separating of the light phase oil material and the aqueous phase mixture from the stillage also produces a phase having a greater amount of suspended solids than the aqueous phase mixture.

In an embodiment of the eighth aspect, the stillage is concentrated thin stillage.

In an embodiment of the eighth aspect, the recovered compounds are selected from the group consisting of organic acids, fatty acids, glycerin, peptides, polypeptides, betaines, carbohydrates, and vitamins.

In an embodiment of the eighth aspect, mechanically processing the aqueous phase mixture comprises the use of filters.

In an embodiment of the eighth aspect, mechanically processing the aqueous phase mixture comprises the use of filters, wherein the aqueous phase has a first content of particles greater than about 1000 nanometers, and the clarified aqueous stream has a second content of particles greater than about 1000 nanometers, and the second content is less than about 5% of the first content.

In an embodiment of the eighth aspect, mechanically processing the aqueous phase mixture comprises the use of filters, wherein the aqueous phase has a first content of particles greater than about 200 nanometers, and the clarified aqueous stream has a second content of particles greater than about 200 nanometers, and the second content is less than about 5% of the first content.

In an embodiment of the eighth aspect, light phase oil material is mechanically and thermally processed to recover essentially oil from the light phase oil material.

In an embodiment of the eighth aspect, light phase oil material is chemically and mechanically processed to recovery essentially oil from the light phase oil material.

In an embodiment of the eighth aspect, light phase oil material is chemically and mechanically processed to recovery essentially oil from the light phase oil material, and the chemical processing of the light phase oil material comprises the addition of basic, ionic salt solution of sodium hydroxide wherein the concentration of the sodium hydroxide solution is between about 1% and about 99% sodium hydroxide by weight.

In an embodiment of the eighth aspect, the recovered compounds comprise at least one organic acid.

In an embodiment of the eighth aspect, the recovered compounds comprise at least one organic acid selected from the group consisting of succinic acid, lactic acid, and acetic acid.

In an embodiment of the eighth aspect, the mechanically separating step is performed on the concentrated stillage at a temperature of between about 140° F. and about 212° F.

In an embodiment of the eighth aspect, the mechanically processing step comprises, in sequence, a centrifugal clarification and a filtration step.

In an embodiment of the eighth aspect, the recovery of compounds is performed by a solid phase, adsorbent separation process.

In an embodiment of the eighth aspect, the recovery of compounds is performed by a solid phase, adsorbent separation process, wherein the solid phase adsorbent separation process comprises a regenerative adsorbent bed or simulated moving bed process.

In an embodiment of the eighth aspect, the recovery of compounds is performed by a solid phase, adsorbent separation process comprising an ion exclusion or ion adsorption resin material.

In a ninth aspect, a method of recovering compounds from stillage is provided, the method comprising, in sequence: evaporating and mechanically processing the stillage to create an aqueous phase mixture and a light phase oil material, wherein the light phase oil material has a moisture content of greater than 5% by weight and a lipid composition of greater than about 50% by weight on a dry basis; and recovering compounds from the aqueous phase mixture by mechanically processing the aqueous phase mixture, and creating a clarified aqueous phase mixture.

In an embodiment of the ninth aspect, the aqueous phase has a first content of particles greater than about 1000 nanometers, and the clarified aqueous stream has a second content of particles greater than about 1000 nanometers, and the second content is less than about 5% of the first content.

In some embodiments, at least 10% weight of the stillage is the light phase oil material or as otherwise described herein.

In an embodiment of the ninth aspect, the step of mechanically processing the aqueous phase mixture comprises use of a filter.

In an embodiment of the ninth aspect, the step of mechanically processing the aqueous phase mixture comprises use of a clarifying centrifuge followed by a filter.

In an embodiment of the ninth aspect, the step of mechanically processing the aqueous phase mixture comprises use of a clarifying centrifuge followed by a filter, and recovering compounds comprises the use of a solid phase adsorbent material and a regenerative adsorbent process such as a simulated moving bed.

In a tenth aspect, a method of recovering compounds from stillage is provided, the method comprising, in sequence: heating and evaporating the stillage to create a low volume concentrate with a moisture content of less than about 85% and greater than about 50% by weight; mechanically separating the low volume concentrate into an aqueous phase mixture and a light phase oil material; and recovering compounds from the aqueous phase mixture using chromatography.

In some embodiments, at least 10% weight of the stillage is the light phase oil material or as otherwise described herein.

In an embodiment of the tenth aspect, light phase oil material has a moisture content of greater than about 5% by weight and a lipid content of greater than about 50% by weight on a dry basis.

In an embodiment of the tenth aspect, the recovered compounds include at least one of the following glucose, mannose, xylose, arabinose, succinic acid, lactic acid, glycerin or acetic acid.

In an embodiment of the tenth aspect, the mechanical separating comprises separating a portion of the low volume concentrate as a light phase oil material using a centrifuge.

In an eleventh aspect, a method of processing whole stillage is provided, the method comprising: recovering thin stillage from whole stillage, the thin stillage including high value compounds, lipids and solids; heating and mechanically processing the thin stillage to produce a light phase portion of the thin stillage with a moisture content greater than about 5% and less than about 50% by weight and an aqueous phase portion; mechanically processing the aqueous phase portion to recover compounds; and recovering oil from the light phase portion.

In some embodiments, at least 10% weight of the stillage is the light phase oil material or as otherwise described herein.

In a twelfth aspect, a method of recovering compounds from an aqueous stream is provided, wherein the aqueous stream was generated by separating a light phase oil material and an aqueous stream from a stillage stream, and the light phase oil material was further processed to recover oil by a process comprising chemical or evaporative treatment of the light phase oil material.

In some embodiments, at least 10% weight of the stillage is the light phase oil material or as otherwise described herein.

BRIEF DESCRIPTION OF THE DRAWINGS

FIG. 3a is an illustration of a process to separate a light phase mixture from stillage with subsequent separation of oil with chemical treatment and optional separation of aqueous compounds including additional pretreatment and post-treatment steps.

FIG. 7 is a graph of the titration curves for concentrated thin stillage, light phase materials.

FIG. 8 is a tabulation of results for samples from different points in a process utilizing chemical post treatment showing the separation of phases achieved.

DETAILED DESCRIPTION OF THE INVENTION

Introduction

Figure 1:
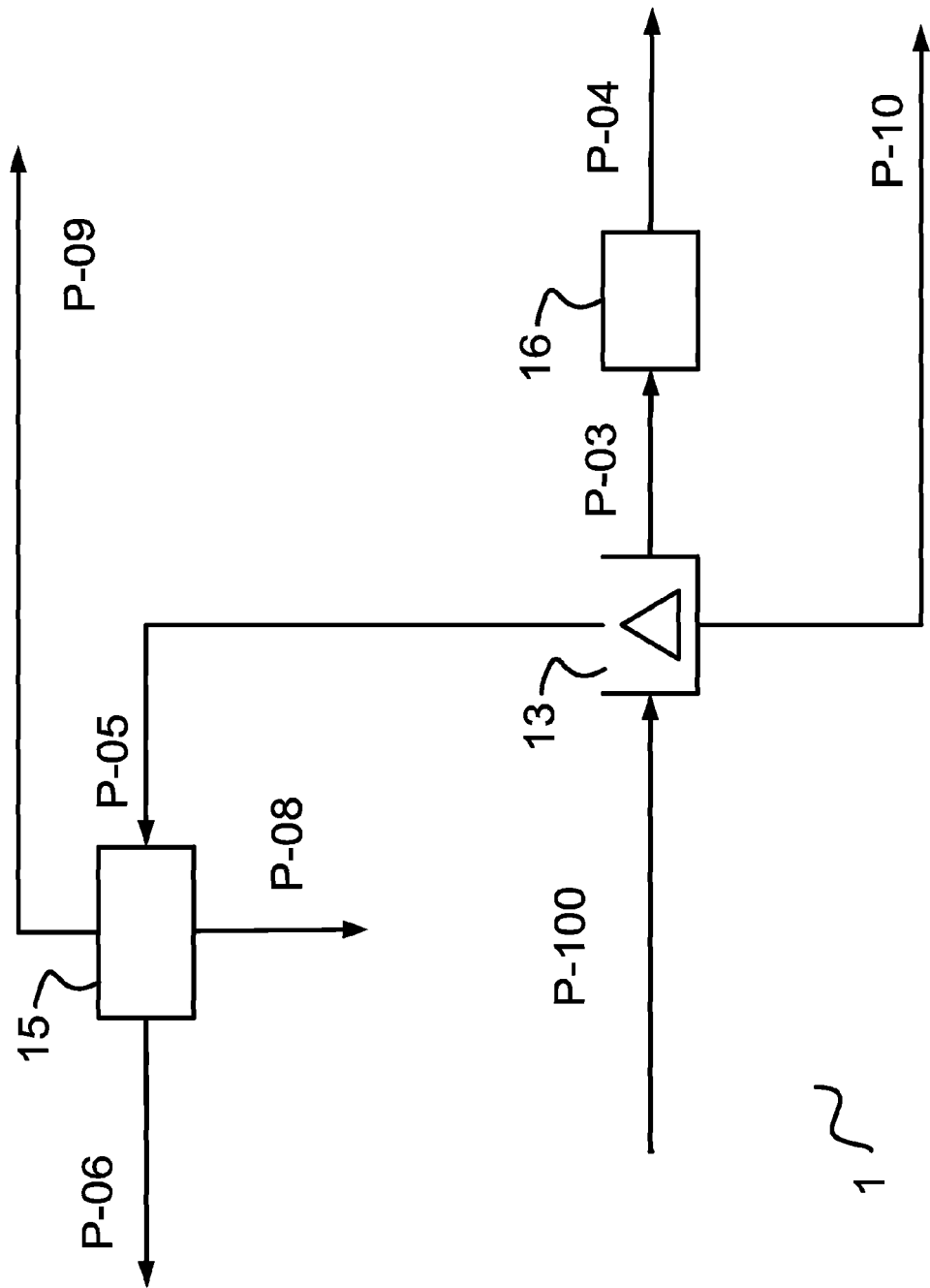
FIG. 1 is an illustration of a process to separate a light phase mixture from stillage with subsequent separation of oil and optional separation of aqueous compounds.

The following description and examples illustrate some exemplary embodiments of the disclosed invention in detail. Those skilled in the art will recognize that there are numerous variations and modifications of this invention that are encompassed by its scope. Accordingly, the description of a certain exemplary embodiment should not be deemed to limit the scope of the present invention.

Fermentation processes can frequently utilize lipid-bearing substrates. Examples of such substrates can include dry-milled grains with relatively high oil content, such as corn or milo; other grains with oil content, such as barley, rye, or wheat; leguminous materials, such as soybean, and lentil products; and other materials such as tree products and animal products. These substrates can be used during the production of alcohol, organic acids, acetone, butanol or other products that are removed from the fermentation broth by a process comprising distillation or evaporation of the product. The remaining material after distillation or evaporation, the "stillage," can then be treated to recover residual oil and/or other desired products from the stillage. Other desired products can include, but are not limited to, organic acids, lipids or oils, glycerin, sugars, proteins, amino acids, soluble/insoluble fiber including polysaccharides and oligosaccharides, and others. Examples of organic acids that can be recovered, depending on the particular fermentation and the micro-organisms involved, include acetic, lactic, succinic, oxalic, citric, malic, formic, propionic, butyric acid, and others.

In one embodiment, dry-milled corn can be used to produce ethanol with subsequent recovery of oil and/or other compounds in addition to the ethanol. Corn processed in a dry grind ethanol facility can have between about 3 to about 5% (wt.) oil on a dry basis. In such a facility, the production process can include milling of the corn, treating the milled corn with enzymes to hydrolyze starches to shorter saccharides ("liquefaction"), further breakdown of the saccharides into monomeric sugars ("saccharification"), fermentation of the sugars and some other saccharides by yeast or other appropriate organisms, distillation to recover ethanol, dehydration to remove residual water from ethanol, and/or handling of the remaining stillage.

Oil present in the corn germ can, in some cases, be fully or partially liberated from the corn's germ during the upfront processing steps, such as liquefaction, before the mixture is added to the fermentors, or during processing within the fermentor, such as during the fermentation itself. This liberated oil can function as a non-fermented/partially fermented, non-reactive/partially reactive de-foaming agent in the fermentation reactors with at least a portion ultimately passing through the ethanol distillation process into the whole stillage. This whole stillage (typically less than about 15% (wt.) dry matter solids) is frequently stored in a whole stillage tank and then processed by decanter centrifuge, to separate solid matter ("wet grains") (typically greater than about 30% (wt.) dry matter solids) from a centrate stream (typically less than about 10% (wt.) dry matter solids). Frequently, approximately 20 to 40% (wt.) of the oil in the feed corn passes out with the wet grains, which also can represent about 50% (wt.) of the total dry matter. In some facilities, the centrate stream is divided into a backset stream, which is returned to an earlier point in the process for reuse in the fermentation and a "thin stillage" stream, which is processed in an evaporator train or otherwise concentrated to remove water and concentrate the residual material to "syrup." Syrup or concentrated stillage can in some embodiments have a moisture content of about 50% to about 85% (wt.), or about 50% to about 80% (wt.), or about 55% to about 70% (wt.), or about 55% to about 60% (wt.). For the sake of this description, the stream will be described as thin stillage throughout the evaporators, and only as syrup at the end of the evaporation train. Frequently, the syrup will have a dry mass concentration of about 30 to about 40% (wt.). Generally, very little non-moisture compounds are carried out of the evaporators with the water vapor or overheads, which results in a linear decrease in liquid flow rate as the moisture is evaporated and oils and solids are concentrated. Frequently, the wet grains and syrup are dried together or separately to make various products such as "dried distillers grains," ("DDG") or "dried distillers grains with syrup" or "dried distillers grains with solubles" ("DDGS"). In some cases, such as where the feed products are locally marketed and a short storage life is tolerable, the feed can be dried to about 50 to about 60% (wt.) moisture and referred to as modified feed. When longer storage life is desired, the moisture content is reduced to about 8 to about 20% (wt.). The actual values for concentrations and mass balances will vary from plant to plant based on operating parameters, particular equipment, operating conditions, and specific equipment capacities.

Description of Evaporator Trains

At least two different configurations of commercial dry-grind, fuel ethanol facilities are in use today based on the design and operation of the post distillation evaporator train. In two common types of facilities, the fermentation mash is passed to a distillation column for the removal of product ethanol and then solids are partially removed from the stillage and this "thin stillage" is passed to an evaporation train for concentration of the thin stillage into "syrup." Although there are many differences in the operational characteristics, one primary difference is the cascading of the thermal energy between the distillation and evaporation processes, which results in "Type A" facilities having an evaporation process operated at higher temperatures and pressures, frequently with at least a portion of the process operating at about 180° F., while the other, "Type B" facilities, have an evaporation process operated at lower temperatures and pressures, generally about 145° F. In some cases, the higher temperature Type A systems have been reported to allow recovery of a small amount of the oil present in the stillage after evaporation. While not wishing to be bound by theory, it is believed that the impact of the higher temperature evaporation is the partial liberation of lipids from the emulsions and/or the solids-oil suspensions present in the complex stillage mixtures. However, only a portion of the oil present is liberated in the Type A facility evaporator train, and little or no oil is liberated in the Type B facility evaporator train. As a result, mechanical processing, such as by processing comprising mechanical separation, for example centrifugation or another mechanical separation technique, but without chemical treatment or solvent extraction as a part of the mechanical processing step itself, of the syrup without additional processing steps can only recover a fraction of the oil present in Type A systems, and none or virtually none of the oil in Type B systems. In various embodiments, methods are provided that provide high recovery of lipid materials from both Type A and Type B ethanol facilities, as well as other types of ethanol and other fermentation product facilities where it is desired to recover lipids/oils from a post-fermentation stream such as a stillage stream. In some embodiments, the methods presented can be used where stillage streams have a high degree of emulsions and oily solid suspensions and very little free oil compounds.

In some embodiments, the removal of lipids/oil from the stillage can be combined with the recovery or separation of products from an aqueous byproduct portion of the stillage. In some embodiments, the reduced oil/lipid content of the stream can result in improved recovery efficiency and improved operation of the separation/recovery of products from the aqueous stream.

Utilization of the grains (wet grains, distillers dried grains, DDG, or DDGS) and stillage in the animal feed market generally results in a low value product, and might be sold in today's market at about 5-10 cent per pound (dry basis). In comparison, a crude oil product recovered from the stillage or distillers grains can have a market value of about 20-40 cents per pound, and other compounds present in the stillage as soluble compounds, such as organic acids and glycerin, can have values of about 10 to 20 times greater.

Separation of a Light Phase Mixture from Stillage with Subsequent Oil Recovery

In one embodiment, as shown in FIG. 1, a process for recovering oil P-09 from stillage P-100 can include a separation step 13, and a post-treatment step 15. In some embodiments, an optional aqueous treatment step 16 to recover other desired products can be combined with the process for recovering oil, and an optional temperature adjustment step can be added to the feed for the separation step 13. The stillage P-100 can be whole stillage, thin stillage, a concentrated thin stillage such as syrup, or some combination thereof.

In some embodiments, stillage can be separated into three or four phases or layers that can form during separation, such as with a laboratory or commercial centrifuge or a filtration system, and are referred to as free oil, light phase, aqueous phase, and solids.

Free Oil—includes an oily material having the appearance and consistency of oil or crude oil; the phase can be clear, translucent, opaque, or some intermediate level of these characteristics. In some embodiments, the free oil can have less than about 5% (wt.) non-oil dry matter or nonsaponifiable dry matter, and in some embodiments, less than about 4% (wt.) non-oil dry matter or nonsaponifiable dry matter, while in some embodiments, the free oil has less than about 2% (wt.), or less than about 1% (wt.), non-oil dry matter or nonsaponifiable dry matter.

Light Phase—includes a phase having specific gravity intermediate between the free oil phase and the aqueous phase. In some embodiments, the light phase has a specific gravity smaller than 1 (e.g., when measured at room temperature). As defined herein, the light phase is characterized by the inclusion of emulsions of an aqueous phase and an oil/lipid phase. In some embodiments, the light phase is composed of emulsions of oil/lipid and water (e.g. aqueous solution). In some embodiments, the light phase additionally includes solid material in the emulsions. Therefore, the specific gravity of the light phase varies based on its composition. In some embodiments, the light phase comprises one single emulsion layer. In some embodiments, the light phase comprises two or more emulsion layers, each having a different specific gravity.

Aqueous—includes a phase comprising an aqueous continuous phase which can have dissolved or entrained species, (solid, liquid, and/or gas) present. Frequently, it can appear as a thin aqueous continuous phase with a small amount of other suspended material. The overall material can generally have a specific gravity close to 1 when measured at room temperature, but which can vary to some extent due to the additional species present.

Solids or Bottom phase—includes a solid or semisolid pellet or sludge that can be thicker than the other phases. The overall solids material will generally have a specific gravity larger than 1 when measured at room temperature, but which can vary to some extent due to the additional species present.

With some feed streams, not all four phases will be present, depending on the actual composition of the material and the affinity of various species for others. In one embodiment, the free oil phase can be absent or vanishingly small due to various reasons, such as the oil is sufficiently associated with solids, water, or other components of the other phases to be incorporated into one or more other phases. In some embodiments, during operation two or more of the phases can be collected together, such as when a feed stream if centrifuged with a laboratory centrifuge would form four layers but a commercial centrifuge is used to separate only one fraction from the rest of the material, such as where the centrifuge is used to recover the free oil and light phase fractions as one stream and the aqueous and bottom faces as another stream, or the free oil as one stream and the light, aqueous, and bottom phase together as a second stream, or the free oil, light, and aqueous phases together as one stream and the bottom phase as a second stream. In embodiments where a separate free oil phase is not collected, but either the oil is incorporated into other phases or the free oil and light phases are collected together, the lightest fraction collected can be referred to as a "light phase mixture." The term "light phase oil material" refers to material that can be either light phase or light phase mixture or combinations thereof.

In some embodiments, a commercial centrifuge or other separation device can be used to separate the feedstream into two outlet streams and one or both of those outlet streams or portions thereof can optionally be separated into two or more streams with subsequent processing, such as with a centrifuge. In some embodiments, a commercial centrifuge can be used to separate a feedstream into three discharge streams, such as where only three of the phases are present or where two of the streams are collected together, such as the free oil and light phases or the aqueous and bottom phases. In some embodiments, the separation achieved by a centrifuge can occur within one of the phases rather than at an interface between two of the phases, such as where a centrifuge divides one of the phases, such as the oil, light, aqueous, or bottom phase between two discharge streams. In some embodiments, the separation achieved by a centrifuge can occur at the interface between two of the phases, such as where the first phase is entirely or nearly entirely routed into a first discharge stream and an adjacent phase is routed to any second stream with little or no of the second phase being present in the first discharge stream.

In some embodiments, a separation into phases can be accomplished using filters, such as where larger particles can be separated with a coarser filter medium, and represent a material analogous to the bottom phase; a finer filtration medium can separate a thin aqueous material from a more oil rich material retained by the filter, with the thin aqueous material being analogous to the aqueous phase, and the oil rich material being referred to as light phase and/or light phase mixture; and a free oil fraction can be separated from a fraction having a greater moisture content based on, for example, differing affinity of the water or oil to the filtration medium and/or globules or associations of oil, water, and/or solid having impaired passage through the filter medium.

In some embodiments, a crossflow filtration system, such as a microfilter, nanofilter, or reverse osmosis system can be used to affect one or more of these separations, and such systems can advantageously utilize medium of varying hydrophilicity, hydrophobicity, surface charge and/or other surface affinity.

Likewise, a similar separation can be accomplished in some embodiments with settling or decanting equipment, with gravity causing the feed stream to separate into layers, phases, or regions of different specific gravity with the lowest specific gravity material generally above higher specific gravity material. In some embodiments, the specific gravity change between the material designated as the different phases can be a stepwise change, in some embodiments, it can be more gradual, and in some embodiments it can be a combination of the two.

Separation Step 13

Separation step 13 can utilize any appropriate technology to separate the stillage P-100 into a lipid rich phase P-05 and one or more streams that include the remainder of the feed. In some embodiments, separation step 13 can separate the stillage P-100 into a lipid rich phase P-05, a predominantly aqueous phase P-03, and a predominantly solid phase P-10. Suitable technologies for separation step 13 include mechanical separations, such as those utilizing differences in density and differences in size, such as decanting vessels, centrifuges, filters, etc. as well as combinations of these technologies. In some embodiments, one or more decanting vessels can be used to separate a heavier solids-rich phase from an intermediate predominantly aqueous phase and a lighter lipid-rich phase. In some embodiments, the separating step 13 can utilize a decanting vessel, a tri-phase centrifuge, or multiple step filtrations.

In some embodiments, the separation can be made with one or more centrifuges. Suitable centrifuges can include decanter centrifuges, disc stack centrifuges, basket centrifuges, tubular centrifuges, auto-desludging centrifuges, nozzle centrifuges, solid disk decanters, etc. In one embodiment, an auto-desludging, disk stack centrifuge such as the Westfalia RS-220 series can be used.

Centrifuges, filters, or other separation devices can be continuous, semi-continuous, or batch operated. In some embodiments, a centrifuge, filter, or other separation device can divide a feedstream P-100 into two outlet streams. In some embodiments a centrifuge, filter, or other separation device can divide a feedstream into two or more outlet streams. In practice, two or more centrifuges, filters, or other separation devices can be installed in series, such as to provide tighter separation of outlet streams, or to divide a product stream into two or more additional streams, such as where a first centrifuge, filter, or other separation device separates a lipid rich phase P-05 from the remainder of the feed, and a second centrifuge, filter, or other separation device separates the remainder into a predominantly aqueous phase P-03 and a predominantly solid phase P-10. In practice, two or more centrifuges, filters, or other separation devices can be installed in parallel, such as to provide additional capacity, better separation, etc. When multiple centrifuges, filters, or other separation devices are installed in series or parallel, the resulting streams from different centrifuges, filters, or other separation devices can be combined to achieve desired results.

Separating step 13 can be adjusted or operated to generate a light phase mixture P-05 with a moisture content less than a feed material. In some embodiments, the entire volume of P-05 will have the appearance of a cream or an emulsion. In some embodiments, the entire volume of P-05 can exhibit an elevated viscosity as compared to the other separated fraction P-03. In some embodiments, an additional fluid and/or solid phase can be present with material having a creamy or emulsified or viscous appearance. In some embodiments, P-05 can have a moisture content of greater than about 3% (wt.), or greater than about 5% (wt.), or greater than about 10% (wt.), and in some embodiments, the moisture content can be in the range of about 5% (wt.) to about 50% (wt.) or about 5% (wt.) to about 30% (wt.) or about 10% (wt.) to about 30% (wt.) or about 10% (wt.) to about 25% (wt.) or about 5% (wt.) to about 25% (wt.). In some embodiments, P-05 can comprise a mixture of solid/air/oil suspension, high lipid-water mixtures, and/or oil-solid suspension. In some embodiments, P-05 can have sufficient moisture for the post-treatment step 15 chemical/pH treatment and/or evaporation/thermal treatment to modify the structure of the material present to facilitate the recovery of free oil product.

In some embodiments, P-03 can have an oil content of greater than about 40% (wt.), or greater than about 50% (wt.), or greater than about 60% (wt.) or greater than about 70% (wt.), or greater than about 80% (wt.). In some embodiments, the separation of light phase mixture stream P-05 can help to reduce the content of non-soluble lipid compounds in the aqueous phase stream P-03. By reducing the non-soluble lipid content of P-03, the operation of any downstream operations on the aqueous phase mixture P-03, including but not limited to optional aqueous post-treatment step 16 can, in some embodiments be improved.

Separating step 13 can also be adjusted or operated to obtain a solids level of the solids-rich stream P-10 of about 30% (wt.) to about 60% (wt.) or about 35% (wt.) to about 45% (wt.). In some embodiments, the composition of stream P-05 can be monitored and controlled with the composition of the remainder stream or of stream P-10 or stream P-03 allowed to change. In some embodiments one of these other streams can be monitored and controlled while the composition of stream P-05 is allowed to change. In some embodiments, more than one of these streams are monitored and controlled.

In one embodiment, separation step 13 can be set up and operated to provide a light phase mixture stream P-05, that includes low specific gravity components of the feed to separation step 13. In one embodiment, stream P-05 can have a specific gravity below about 1.03. In some embodiments, stream P-05 can have a specific gravity below about 1.0. In some embodiments, stream P-05 can have a specific gravity below the bulk specific gravity of the aqueous phase stream P-03, or P-10, or P-100, or P-03 and P-10 combined. In some embodiments, stream P-05 can have a specific gravity below about 1.03 and less than the specific gravity of P-100.

In some embodiments, the separation step 13 can be set-up and operated to separate a light phase mixture P-05 having a specific gravity greater than the specific gravity of the free oil product stream P-09, as measured at process temperature. In some embodiments, the specific gravity of stream P-05 can have a specific gravity less than that of P-09, which has less than about 1% (wt.) water and less than about 2% (wt.) non-oil dry matter or unsaponifiable matter. In some embodiments, the light phase mixture will have a specific gravity of about 0.85 and 0.95 at 180° F., or a specific gravity of about 0.88 to about 0.92 at 180° F., or a specific gravity of about 0.90 to about 0.92 at 180° F. In some embodiments, stream P-05 can have a specific gravity of about 0.90 to about 1.1 at room temperature. In some embodiments, stream P-05 can have a specific gravity of about 0.92 to about 1.1 at room temperature. In some embodiments, stream P-05 can have a specific gravity of less than about 1.0 at room temperature. In some embodiments, stream P-05 can have a specific gravity of about 0.90 to about 1.0 or about 0.92 to about 1.0 at room temperature. In some embodiments, stream P-05 can have a specific gravity of about 0.90 about 0.98 or about 0.92 to about 0.98 at room temperature. In some embodiments, the light phase mixture P-05 can have a specific gravity at the desired operating temperatures of between about 0.92 and about 1.0.

Various methods can be used to achieve these moisture contents, compositions, and specific gravities, depending on the separation device being used. For example, with a centrifuge, mechanical changes to the differential speed, dams, pond depth, disk stack design/configuration, basket screen characteristics, partial or full discharge characteristics, timing sequences, etc. as well as operational changes to the rotational speed, feed rate, back pressure, discharge parameters, timing, etc. can be used to change the outlet stream composition. With a filtration system, both crossflow and dead-end type filters, medium pore size, flow rate, transmembrane pressure, medium characteristics (for example, type of filter aid, particle size, charge characteristics, chemical characteristics, fabric weave, etc.), filtration area, pressure drop, etc. can be can be varied, as appropriate, for the particular filter system being used. With a decanting tank, the geometry of baffles, flow rates, and tank size can be used to change the outlet stream composition.

Optional Temperature Adjustment of P-100

In some embodiments, the pretreated feed stream P-100 can be conditioned by adding or removing thermal energy thereby adjusting the temperature of the stream to enhance the specific gravity differences between the various phases of interest. Chemical pretreatment can also be used to change the physical binding characteristics, solubility, and specific gravity difference of the mixture of compounds in the feed stream. In some cases, chemical pretreatment can assist in liberating oil from the oil-solid-water suspensions in P-100, but treatment of the stream can require more reagent and treatment of, for example P-05, and the presence of the additional reagent, and in some cases side products, can adversely impact downstream processes and products.

Reduction or elimination of the non-soluble lipid compounds can improve downstream post processing step 16, which can include methods comprising centrifugal clarification, filtration, and recovery or separation of desired compounds.

Post-Treatment Step 15

The post-treatment step 15 treats the light phase mixture P-05 to facilitate separation and separate a material P-09 that is primarily free oil from the oil-solid-water suspension that exists in the light phase mixture P-05, such as a material that is more than about 95% (wt.) free oil, or more than about 98% (wt.) free oil, or more than about 99% free oil, or a material that consists essentially of free oil, or a free oil material substantially free of other components. In some embodiments, P-09 can have less than about 2% (wt.) water. In some embodiments, P-09 can have less than about 2% (wt.) non-lipid solids. The post-treatment step 15 can comprise separation of the incoming stream into three outlet streams: a vapor stream P-06, a lipid-rich light phase P-09, and a solid-matter-rich heavy phase P-08. Post-treatment step 15 can also include evaporation and/or chemical treatment prior to the separation in order to facilitate separation of an oil or lipid product from the light phase mixture P-05.

Suitable separation equipment and techniques include mechanical separation techniques such as those described above for separation step 13, and include gravity settling, centrifugation, filtration, etc. In various embodiments, equipment and operating conditions can be adjusted to fit the characteristics of the stream being separated, such as temperature, pressure, nature of solids present, specific gravity of stream components, etc. In one embodiment, that can be used with evaporation is venting which allows separation of the generated vapor stream to disengage from the remaining liquid or liquid/solid stream. In some embodiments, venting can take place in an evaporator or in a separate device such as a separation tank, cyclonic separator, or centrifuge. In some embodiments, the vapor separation can take place in the same device as the separation of a lipid-rich light phase P-09 from a solid-matter rich heavy phase P-08. In embodiments that can be used with a chemical treatment step, such as with the addition of a pH modifying agent, depending on the specific characteristics of the light phase mixture P-05 present, the chemically treated/pH adjusted stream can be separated by one or more decanter type clarification vessels or through gravity or forced separation such as with one or more clarifying centrifuges.

Evaporation Treatment

In one embodiment, water can be evaporated from stream P-05. While not wishing to be limited by theory, it is believed that initially during evaporation, only free water is removed which only increases the solids concentration, followed by evaporation of water from the moist solids which causes a restructuring of the solids that forces the lipid compounds free of the oil-solid-water suspensions. One embodiment can include addition of heat with evaporation of water from the light phase mixture P-05. In another embodiment, the pressure of stream P-05 is reduced to cause evaporation of water from stream P-05 with the necessary heat supplied by stream P-05 itself, resulting in a cooling of the stream. In yet another embodiment, both lower pressure and addition of energy to maintain the stream temperature or manage the level of temperature loss or increase the temperature of stream P-05. In each of these embodiments, the light phase mixture is converted into a vapor phase, free oil phase, and semi-dried solids phase, which can be separated by gravity in a decanter vessel, or by additional centrifugal forces. The mixture after post-treatment can be separated into an off-gas stream P-06 (vapor phase), post-treatment bottoms stream P-08 (semi-dried solids phase), and a light phase product stream P-09 (substantially free oil phase), which can be generated, and these streams can be separated or mixed.

The evaporation step can include heating to a temperature greater than about 100° C. such that at least a portion of the moisture content within the solids in the oil-solids-water suspension of P-05 is vaporized to generate an off-gas stream P-06 comprising primarily water vapor. Other gases and volatile/volatizable materials present in the P-05 mixture as well as entrained liquids and/or solids and an oily mist can also be contained in the off-gas stream P-06. The pressure at which the post-treatment process 15 takes place can be adjusted to facilitate vaporization of the moisture content of the solid material in the light phase mixture. In some embodiments, the target temperature of the light phase mixture in the post-treatment process is greater than about 80° C. and less than about 150° C., or between about 105° C. and about 120° C., or between about 108° C. and about 118° C. The equipment in the post-treatment step can be any suitable device, such as a heater, heat exchanger, falling film evaporator, direct steam injection heater, microwave energy source, or any other equipment that can raise the temperature of the light phase mixture to the target temperatures. Heating and evaporating the light phase mixture P-05 can be less prone to fouling in comparison to heating and evaporating of stillage, such as when indirect heating is utilized. As a result, higher temperatures, higher final solids levels, and/or higher evaporation rates can be utilized to process P-05 in post-treatment step 15 than would be possible for stillage. In addition, in some embodiments, product oil or oil rich stream P-09 can be re-circulated to post-treatment step 15 and mixed with incoming or partially processed P-05 material to create a higher concentration of oily compounds, providing further action against fouling, and in which the energy needed to evaporate the moisture of the light phase material can be added to the re-circulated stream prior to mixing with the stream in post-treatment step 15. Microwave energy sources can be used to provide indirect heating of the light phase mixture stream. The target temperature range can be set to drive the water vapor from the solids in the mixture, which dehydrates the small particles and forces the oil-solid suspension to breakdown releasing the oil as free oil. If lower pressures are applied to the light phase mixture P-05 by applying a vacuum in post-treatment step 15, lower temperatures can be utilized and temperatures under about 100° C. are feasible. These lower pressures can be achieved by any suitable method, such as by using an eductor, jet pump, or vapor compression device in the feed stream as part of the pretreatment step 12. Some exemplary results of this post-treatment technique are provided in later examples.

Chemical Treatment

Various chemical treatments can be utilized to facilitate separation of oil from the oil-rich material of P-05. In one embodiment, of chemical treatment, the pH of stream P-05 can be adjusted to an appropriate range to enhance the separation of oil from stream P-05. In some embodiments, the pH is adjusted to at least about 6, 6.5, 7, 7.5, 8, or 8.5. In some embodiments, the pH is adjusted to a value less than 11, 10, 9, 8, or 7. In some embodiments, the pH is adjusted to a range of about 6 to about 7, about 6 to about 7.5, about 6 to about 8, about 6 to about 9, about 6 to about 10, or about 6 to about 11. In some embodiments, the pH is adjusted to a range of about 6.5 to about 7, about 6.5 to about 7.5, about 6.5 to about 8, about 6.5 to about 9, about 6.5 to about 10, or about 6.5 to about 11. In some embodiments, the pH is adjusted to a range of about 7 to about 7.5, about 7 to about 8, about 7 to about 9, about 7 to about 10, or about 7 to about 11. In some embodiments, a suitable pH range can be determined by performing a bench test of a sample of stream P-05, such as by adjusting the pH of the material and observing resulting behavior of the solids and/or oil, such as by observing flocculation/coagulation/precipitation, oil formation, oil collected, using a turbidimeter or nephelometer, or by other appropriate observations. In some embodiments, a titration test for a sample of P-05 can be performed and a pH range or amount of pH adjusting reagent can be determined based on the titration results. In one embodiment, a pH range or amount of pH adjusting reagent can be determined which achieves a pH or dosage of reagent in the vicinity of an inflection point or discontinuity in the titration curve. In some embodiments, the adjustment of pH can be achieved while the solid material still contains at least sufficient moisture to facilitate the transport of charges or to facilitate a pH related reaction. In some embodiments, chemical treatment can include a feedback measurement of the pH of the post treated stream. In some embodiments, a process can include a dosing pump to adjust one or more chemical reagents and a static or motorized mixer to ensure rapid and effective mixing of the oil rich material P-05 and the chemical reagent. Downstream of the static mixer can be a pH sensor which is used to adjust the rate of chemical reagent addition with changes in process feed stream characteristics. With variable oil rich material P-05 characteristics such as flow rate, oil-solid-water suspension concentration, temperatures, chemical reagent strength, and others more complex control scenarios including feedback and feed forward controls can be used. In some embodiments, ratio control can be utilized.

According to the methods of the present invention, chemical treatment can be used in combination with other post-treatment. In some embodiments, chemical treatment can be used in combination with evaporation treatment. For example, the pH of stream P-05 can be adjusted to an appropriate range prior to evaporation treatment. In some embodiments, chemical treatment is used as an alternative to evaporation treatment.

An advantage of chemical treatment (e.g., pH adjustment) at this point, rather than earlier, is that the volume of stream P-05 is much reduced as compared to the volume of stillage or thin stillage. As a result, significantly less material are required to change the pH of stream P-05 at this stage. Therefore, the methods of the prevent invention provides an economical solution to the problem of oil recovery from fermentation stillage.

Pretreated Biomass Particles

As noted in the Examples, the methods described herein further allow improved oil yield as compared to simple centrifugation methods for removing oil. The methods of the prevent invention are particularly advantageous for extracting oil from stillage that, when subject to mechanical separation (e.g., centrifugation 5 minutes at 4000 rpm), can be processed to generate a relatively greater content of light phase oil material. In some embodiments, at least 4%, 5%, 6%, 7%, 8%, 9%, 10%, 11%, 12% weight of the stillage is the light phase oil material. In some embodiments, at least 5%, 6%, 7%, 8%, 9%, 10%, 11%, 12%, 13%, 14% volume of the stillage is the light phase oil material. In some embodiments, less than 10%, 5%, 2% weight of the stillage is aqueous phase mixture. In some embodiments, less than 10%, 5%, 3% volume of the stillage is aqueous phase mixture. In some embodiments, the ratio of the volume of emulsion to free oil is at 1:1, 2:1, 3:1, 5:1, 10:1 or more.

One way to generate stillage having a relatively greater content of light phase oil material is to use pretreated biomass particles having relatively smaller sizes. It has been noted that yield of biofuel (e.g., ethanol) can be improved by using biomass particles having small sizes, e.g., biomass particles having a relatively uniform particle size of less than 1600 microns. For example, at least 95% of the pretreated biomass particles have a particle size from about 100 microns to about 800 microns, or a particle size from about 100 microns to about 500 microns. Methods described herein further allow improved oil yield as compared to simple centrifugation methods for extracting oil from stillage generated from pretreated biomass particles having relatively smaller sizes.

Pretreated biomass particles can be generated by, e.g., a hammer mill or a colloid mill. For example, the colloidal mill can be used to select the resulting particle size distribution through the use of gap rotational controls. A relatively precise particle size distribution can be obtained from much larger biomass material using a colloid mill in contrast to alternative pretreatment techniques such as comminution with a hammer mill. An appropriate gap size on the colloid mill can produce a highly uniform suspension of biomass, where the maximum particle size of the biomass is greatly reduced and significantly more uniform compared to using only the comminution device. The radial gap size for a colloidal mill used in a corn ethanol plant can range from 0.104-0.728 millimeters, e.g., from 0.104-0.520 millimeters, e.g., from 0.208-0.520 millimeters, such that the resulting particle sizes are in the range of 100-800 microns. For example, in some embodiments, a gap setting of 0.1-0.15 is used for corn stover or other cellulosic biomass and a gap setting of 0.2-0.3 mm is used for grains including but not limited to corn kernels.

In some embodiments, the biomass feedstock is corn, corn stover or corn silage.

Description of Aqueous Post-Treatment

Effective desirable product recovery methods can comprise chromatography, distillations, vapor compression distillation, osmotic distillation, micro and nanofiltration, reverse osmosis, and other methods which capitalize on the physical and chemical properties of the various desirable products. The aqueous phase P-103 can be filtered down to 200 nm and desirable products can be recovered using chromatography columns with ion-exchange and ion-exclusion stationary phases. Desirable products P-04, P-104 comprising glucose, mannose, xylose, arabinose, succinic acid, lactic acid, glycerin and acetic acid and others can be recovered. In some embodiments, the use of mechanical separation 13 to initially isolate the light phase material P-05 from the feed stillage P-100, can enhance the effectiveness of the aqueous phase post-treatment. In some embodiments, isolating the lipid rich light phase material can improve the performance of a filtration utilized in some embodiments of an aqueous post-treatment step 16.

Methods for recovery of desirable compounds P-04, P-104 from the aqueous portion of the stillage after recovery of at least a portion of the oil present can comprise any suitable method such as chromatography, adsorption, simulated moving bed chromatography, ion exchange, distillation, vapor compression distillation, osmotic distillation, micro and nanofiltration, reverse osmosis, absorption, and other methods which utilize the physical and chemical properties of the various desired compounds including combinations of these methods.

The term "adsorption process" as used herein is a broad term, and is to be given its ordinary and customary meaning to a person of ordinary skill in the art (and is not to be limited to a special or customized meaning), and refers without limitation to separation processes and combined separation-reaction processes, which include adsorption as a part of the methods being employed. Included are techniques such as in-situ regenerative bed adsorption; chromatography, including simulated moving bed chromatography; and catalyzed reactive bed adsorption.

The term "chromatographic separation" as used herein is a broad term, and is to be given its ordinary and customary meaning to a person of ordinary skill in the art (and is not to be limited to a special or customized meaning), and refers without limitation to rate-based separation of chemical species over a stationary solid phase chromatographic stationary phase by differential partitioning of the species between the stationary phase and a mobile phase. Differential partitioning can occur during the contacting of a process feed stream with a stationary phase, upon contacting a stationary phase having adsorbed species, or both. The effect can be different species exiting the system at different times, or with 5 MB, at different points of the system.

The term "stationary phase" as used herein is a broad term, and is to be given its ordinary and customary meaning to a person of ordinary skill in the art (and is not to be limited to a special or customized meaning), and refers without limitation to a solid phase sorbent of an adsorption process, including the bed or column material in chromatography, the adsorbent material in ion exchange, the adsorbent material in CRB, and the solid phase adsorptive material in adsorbers. Related terms include resin, adsorbent, chromatographic bed material and chromatographic sorbent." The stationary phase material can be utilized in IRB, CRB, and 5 MB systems.

The term "resin" as used herein is a broad term, and is to be given its ordinary and customary meaning to a person of ordinary skill in the art (and is not to be limited to a special or customized meaning), and refers without limitation to stationary phase material, generally, and can include natural and synthetic materials, such as polymeric, zeolites, alumina, silica, and zirconia materials, whether functionalized, derivatized, whether modified or unmodified. In some usages herein, the meaning can be limited to synthetic materials, such as synthetic ion exchange resin or synthetic adsorption resin, with the context indicating a broad or narrow meaning. In some usages herein, the meaning can be limited to zeolites, alumina, silica, or zirconia based substrates, with the context indicating a broad or narrow meaning. In some usages herein, the meaning can be naturally occurring or chemically or physically surface functionalized substrates.

The term "in-situ regenerative bed system" as used herein is a broad term, and is to be given its ordinary and customary meaning to a person of ordinary skill in the art (and is not to be limited to a special or customized meaning), and refers without limitation to adsorptive separation systems where particular species are adsorbed from a material onto a stationary phase, and remain on the stationary phase until treated with a material causing the desorption of the adsorbed species. In some cases, the adsorbed species can be adsorbed from a mobile phase flowing through stationary phase, and the adsorbed species can be desorbed from the stationary phase into a mobile phase. Frequently, a bed is used to adsorb particular species until it is saturated, at which point the saturated bed is removed from the process stream and treated to cause desorption of the adsorbed species and regeneration of the bed. Frequently, the bed will remove virtually all of the species being adsorbed from the mobile phase until the stationary phase is saturated, or until removed from service. In cases where the bed becomes saturated, saturation can be detected by "breakthrough" (a sudden increase in concentration) of the species being adsorbed in the mobile phase exiting the bed.

The term "simulated moving bed chromatography" as used herein is a broad term, and is to be given its ordinary and customary meaning to a person of ordinary skill in the art (and is not to be limited to a special or customized meaning), and refers without limitation to forms of chromatographic separation or other adsorptive processes where, for example, through a valving arrangement, movement of solid phase in a direction opposite of the mobile phase is simulated or accomplished. Frequently, such systems allow for continuous feed streams to be used with resulting continuous outlet streams. The adsorption that takes place in this form of chromatography frequently is a partitioning of adsorbed species from the process feed between a stationary phase and a mobile phase, with adsorbed species being shifted to create portions of mobile phase having higher and lower concentration. Frequently, a chromatographic separation that does not utilize simulated moving bed technology requires interruption of the process feed containing the species to be separated and the timed capture of the various product streams.

Desirable compounds that can be recovered from the aqueous portion of the stillage include organic acids, fatty acids, glycerin, peptides, polypeptides, betaines, carbohydrates, vitamins, enzymes, etc. In some embodiments, organic acids that can be recovered include succinic acid, lactic acid, acetic acid, citric acid, fumeric acid, folic acid, phytic acid, as well as others which can be present in the corn fed to the process, added during processing, or produced during operation.

In some embodiments, fatty acids can include saturated, monounsaturated, and polyunsaturated fatty acids, as well as fatty acids conjugated to a moiety which allows the conjugate to be present in the aqueous stream. Fatty acids can include lauric acid, myristic acid, palmitic acid, stearic acid, oleic acid, palmitoleic acid, vaccenic acid, myristoleic acid, erucic acid, linoleic acid, linolenic acid, arachidonic acid, eicoapentaenoic acid, docosahexaenoic acid, as well as those having a longer or shorter carbon chain, greater or fewer double bonds, double bonds arranged in a cis or trans configuration. In some embodiments, the fatty acid can be conjugated to another moiety, such as with phospholipids, lysophospholipids, monoacylglycerol, diacylglycerol, triacylglycerol, amides, and esters.

In some embodiments, peptides and polypeptides can include amino acids, dipeptides, tripeptides, as well peptides having more than three amino acids. Peptides can be linear or branched.

In some embodiments, carbohydrates can include monosaccharides, disaccharides, oligosaccharides, polysaccharides, each of which can include sugar alcohols as their entire structure or as a portion of their structure. Monosaccharides can have three, four, five, six, or seven carbons. Disaccharides can have two monosaccharides, either the same or different from each other. Oligosaccharides can have three or more monosaccharides, all of which are different from each other, all of which are the same as each other, or some combination of monosaccharides being the same and different from one another. Polysaccharides can have more monosaccharides are present in and oligosaccharides, such as one or more additional monosaccharide. The monosaccharides present in the polysaccharide can be all the same or all different from one another, or some combination of monosaccharides being the same and different from another.

Various methods for recovering or separating the desired compounds, as are known in the art, can be used to recover or separate the desired compounds from the aqueous stream. In some embodiments, the teaching of Kampen in U.S. Pat. No. 5,177,008, issued Jan. 5, 1993, as well as the related patent applications U.S. patent application Ser. No. 381,179, filed Jul. 18, 1989, now abandoned, and Ser. No. 136,415, filed Dec. 22, 1987, now abandoned, all of which are incorporated by reference herein in their entireties for their disclosure related to materials that can be recovered from stillage streams, methods for recovering those products, and the operation of the equipment used in the processing. In some embodiments, a difference in vapor pressure for the desired compound and another component of the stream, including the solvent can be employed to separate with evaporation or distillation. In some embodiments, the charge of a desired compound or another compound present in the aqueous stream can be used to recover the desired product or separate a desired from an undesired compound with ion exchange or chromatography including simulated moving bed chromatography as well as other forms of chromatography. In some embodiments, one or more compounds can be precipitated and then removed from the aqueous stream by, for example, filtration, centrifugation, settling or flotation. In some embodiments, the particle size, molecular weight and/or charge of the compound can be utilized in the separation through such techniques as filtration, centrifugation, settling, flotation, cross-flow microfiltration, nanofiltration, ultrafiltration and reverse osmosis. In some embodiments, a different solvent can be used to absorb the one or more compounds from the aqueous stream. In some embodiments, one or more of these techniques can be combined or used in other ways known to those having skill in the art.

In some embodiments, a process for recovering compounds from an aqueous stream can include clarifying the aqueous stream. Clarification of the aqueous stream can occur simultaneous to, prior to, or after recovery of compounds from the aqueous stream. During clarification the content of larger sized particles present in the aqueous stream can be reduced to less than about 5% of the content in the aqueous stream, or less than about 2%, or less than about 1%, or less than about 0.5%. The reduction of larger size particles can be demonstrated by the reduction in number, weight, or volume of the particles larger than about 3000 nanometers, particles larger than about 1000 nanometers, particles larger than about 500 nanometers, particles larger than about 200 nanometers, particles larger than about 100 nanometers, or particles larger than about 50 nanometers. The reduction can be determined by measuring the amount and/or size of particles in the respective streams by any appropriate technology including measurement of the weight of solid material, diffraction, laser technology, electrical current, etc., and utilizing techniques that include measurement of individual particles, or the properties of a group of particles, and others, as are known in the art, and the comparison can be by concentration or total amount of particles in the size described.

Separation of a Light Phase Mixture from Pretreated Stillage with Subsequent Oil Recovery and Recycle of Streams In one embodiment, the temperature of the feed stream P-100 can be increased to improve the mass transfer and mobility of the compounds and also to enhance the density difference between the lipid containing, suspended solid-liquid-oil emulsions and the bulk aqueous phase materials consisting of suspended and dissolved solids. In some embodiments the temperature of the feed stream P-100 can be increased in a pretreatment step 12 that can be controlled to increase the light-phase stream P-105 volumetric flow rate and lipid concentration. In some embodiments, the degree of pretreatment can be adjusted to not generate an essentially oil product stream with less than about 5% (wt.) moisture content at mechanical separation step 13. Operation of the mechanical separation step 13 can be adjusted to remove substantially all of the lipid containing materials with low specific gravity as light phase mixture stream P-105.

Figure 2:
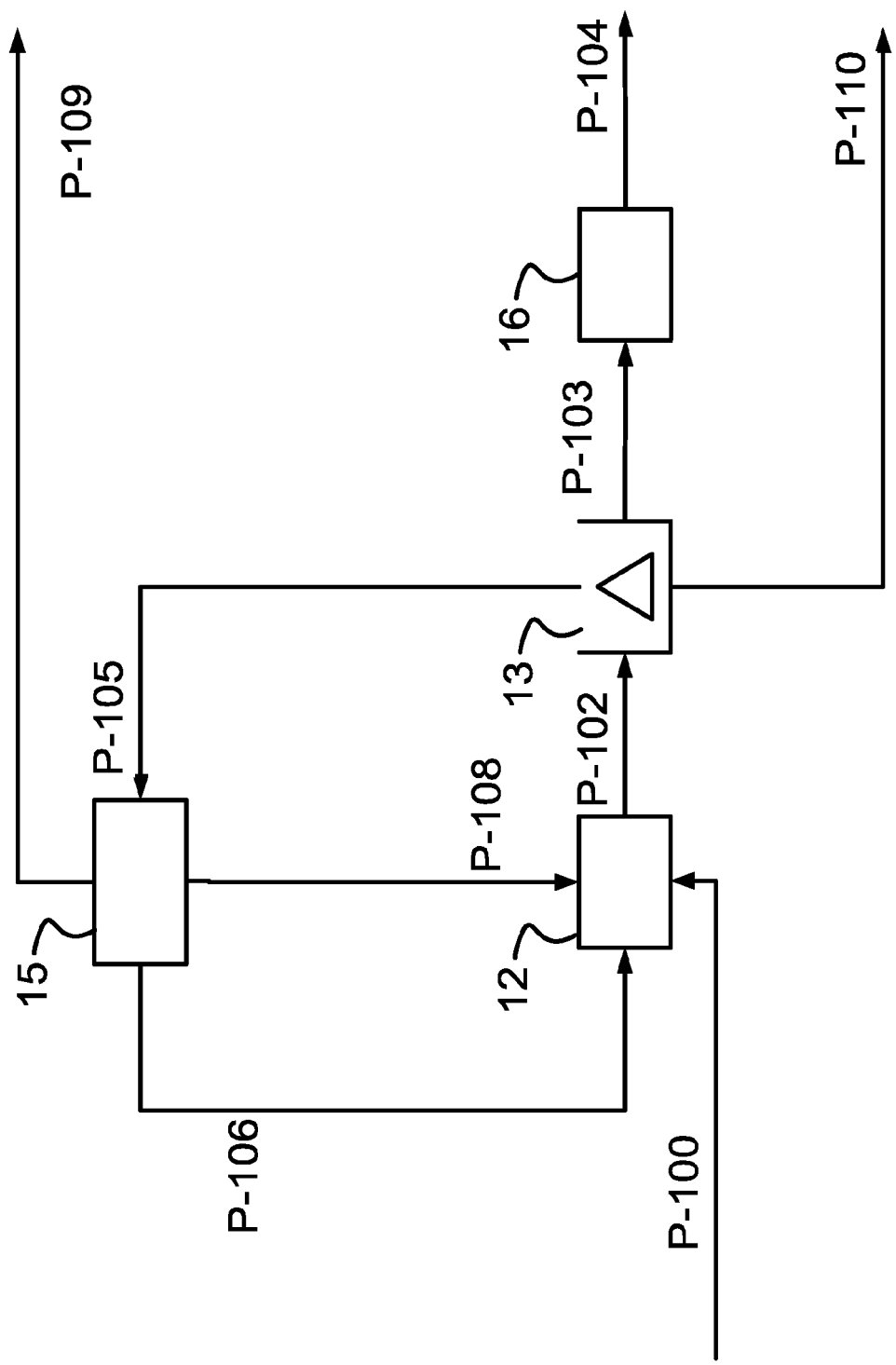
FIG. 2 is an illustration of a process to separate a light phase mixture from stillage with subsequent separation of oil and optional separation of aqueous compounds including a pretreatment step.

In some embodiments, it can be desirable to recycle various streams within the process described above. In one embodiment, as shown in FIG. 2, the off-gas stream P-106 and the bottoms P-108 (corresponding generally to P-06 and P-08, respectively, of FIG. 1) can be passed to the pretreatment step 12 and mixed with the feed stillage P-100 to generate a hot, oil enhanced stillage stream P-102. (The pretreatment step 13, post-treatment step 15, and aqueous treatment step 16 correspond generally to the steps described above, as do streams P-100, P-110, P-103, P-105, P-109, P-104, and P-101 to P-100, P-10, P-03, P-05, P-09, P-04, and P-01, respectively.) The off-gas stream P-106 and bottoms P-108 can be mixed with the stillage stream separately in either order, combined and mixed, or not separated in the post-treatment step and mixed. The technique of mixing these streams and order of mixing these streams into the feed stillage stream is not intended to limit the scope of the innovation. If the post-treatment bottoms stream P-108 is mixed with the feed stream, gentle mixing can be used to reduce emulsification or suspension of the lipids with the bulk stillage. The pretreatment can include the dilution of the feed stillage stream with a hot vapor off-gas stream P-106 from the post-treatment process 15 which can condense when it contacts the feed stillage stream P-100 and increase the temperature of the stillage and specific gravity differences between the various materials. The hot vapor off-gas stream comprises water vapor released from the post-treatment of the light phase mixture P-105. In some embodiments, steam can be used in place of the hot vapor stream P-106 or in combination with it. This hot water vapor of the off-gas stream P-106 and/or steam condenses as it is mixed with the feed stillage P-100. The more dispersed and more uniform heating of the feed stillage stream P-100 increases the temperature of the stillage stream and thereby can increase the specific gravity difference between the oily emulsions/suspensions and the aqueous compounds in the stillage and can improve the separation of the lipid rich materials in the light phase mixture P-105. Additional steam can be introduced with the off-gas vapors, if higher temperatures are desired. In some embodiments, the temperature of the hot, oil enhanced stillage stream P-102 can be less than about 100° C. and greater than about 80° C., and in some embodiments between about 90° C. and about 98° C., and in still other embodiments between about 93° C. and about 96° C. In some embodiments, the bottoms stream P-108 can be added into the stillage stream at pretreatment step 12, or at some other location in stream P-100 or P-102. In some embodiments, including when the bottoms stream P-108 solids are dried sufficiently when mixed with the stillage feed, the solids can be more easily separated as part of the solids phase P-110 in their second pass through the mechanical separation 13. Any bulk free oil phase passed along with the bottoms stream P-108 can coalesce with additional lipid compounds and oil-solid-water suspension into the lower specific gravity phase easily separated with the centrifuge as part of the light phase P-105. In addition, recycle of the solids in stream P-108 provides additional processing to free entrapped oil and other desirable products.

In some embodiments, the recycle of stream P-106 and/or the addition of steam in the pretreatment step 12 or into P-100 or P-120 can allow improved heating of the material fed to the separator step 13. One of the difficulties of processing stillage relates to the use of indirect heating of stillage with heat exchanger surfaces, especially if high temperature, pressure steam is used as the energy source. When steam is used as the hot side heat transfer medium and stillage is the cold side media, the metal surface temperature often exceeds 100 C, which can lead to localized vapor formation on the stillage metal surface. Because of the high solids content of the stillage, this vapor formation can cause deposition of solids on the surface which can build up and foul the heat exchange surface and require excessive clearing or active scraped surface heat exchangers. Recycle of P-106 and/or heating with direct injection of steam provides a more uniform and more dispersed heating of the stillage by the introduction of vaporized water stream and can prevent fouling of heat exchange surfaces and the overheating of the stillage.

Separation of a Light Phase Mixture from Two-Step Pretreated Stillage with Subsequent Oil Recovery with Chemical Treatment and Recycle of Streams In some embodiments, it can be desirable to recycle various streams within the process described above and perform further processing. In one embodiment, as shown in FIG. 3*a*, a chemical treatment step 25 is performed on the light phase material P-105 to facilitate isolation of oil followed by clarification 24 of the pH treated stream P-107 to recover at least a portion of the oil. (The figure reference numbers of FIG. 3*a* generally correspond to those of FIG. 2 where the same number or indicator is used. In addition, post-treatment step 25 and pretreatment step 22 of FIG. 3*a* generally correspond to post-treatment step 15 and pretreatment step 12 of FIG. 2, with differences as noted.) The chemical treatment step can, such as when a base treatment is used, also reduce the free fatty acid concentration of the light phase product P-109. Some example results of this post-treatment technique are provided in later examples.

Generally, separation step 13 can be set-up and operated to create a light phase mixture P-105 as described above, having in some embodiments a moisture content as described above for P-05.

Any basic chemical solution P-120, such as those comprising NaOH, KOH, Na2CO3, etc. can be used to adjust the pH and raise the pH to the range of between about 6 and about 12, between the range of about 6 and about 9, or greater than about 6 and less than about 8. The concentration of the basic solution by weight can be from about 1% (wt.) of the basic material to about 50% (wt.) and as high as saturated solutions and slurries. In some embodiments, solid caustic material can be added to minimize the addition of water to the system. In some embodiments, concentrations of solution include those in the range of about 5% (wt.) to about 50% (wt.). Suitable solutions also include those used for other purposes in an ethanol plant such as a clean in place (CIP) solution used for cleaning equipment having appropriate strength.

The chemical addition of the light phase mixture P-105, including pH adjustment, can be achieved in a single step or in multiple steps using inline static mixers, motorized mixers or batch equipment, and appropriate dosing pumps and/or metering systems. If multiple addition steps are used, the initial step can be a partial adjustment or increase followed by additional steps to provide more accuracy in the level or degree of adjustment achieved with, in some embodiments, various sensors providing control feedback. In some embodiments, a sample can be taken and tested to determine pH, extent of reaction, release of oil, or some other parameter, and the test results can be used in control of the process. In some embodiments, feedback, feedforward, neural network, fuzzy logic, adaptive logic, or some combination of these and other techniques can be used. In some embodiments, a tank, such as a mixing tank, can be utilized for the pH adjustment. In embodiments where a multistep chemical addition or pH adjustment is utilized, after any step of a multiple step adjustment process the process can be followed by a first post-treatment B step 24 in which some or all of the free oil can be removed in P-109 and the balance of the pH treated stream P-107 can be further adjusted or treated or processed or recycled.

The adjustment of pH can be performed while the solid material still has sufficient moisture content to allow measurement of the pH of the mixture. In some embodiments, water can be added with, prior to, or after the addition of one or more pH adjustment materials, and in some cases, residence time can be provided for reaction and/or equilibration of pH.

In still another embodiment, post-treatment A step 25 can include an evaporation step with or upstream or downstream of the pH adjustment. Not wishing to be limited by theory, it is believed that when at least a portion of the moisture present in the solid matter in the stream, rather than the water in the continuous phase of the stream, is removed, the characteristics of the solid matter change which can force oil out of the fine pore structure of the solid matter. Initially, some or all of the water added with the pH adjustment can be vaporized to water vapor P-106 in the evaporative process, before the moisture contained in the solids begins to decrease. Water vapor P-106 can be routed to pretreatment A step 21 and can serve a function similar to stream P-106 and FIG. 2. The concentration of the pH adjustment solution, in some embodiments between about 5% (wt.) and about 50% (wt.) but not limited to these concentrations, can be raised or lowered to help manage the water content of the pH adjusted light phase mixture stream P-107. Also the bottoms of the thermal post-treatment step P-108 can be treated with a pH modifying solution to further enhance oil recovery. In addition, the chemical post-treatment techniques can be combined and integrated in multiple post-treatment and pretreatment approaches depending on the specific characteristic of the light phase mixture and the feed stillage stream.

The pH adjusted mixture P-107 is passed to post-treatment B step 24 where various techniques, including those described for separation step 13 or for the separation step of post-treatment step 15, can be used to recover oil P-109. In one embodiment, the post-treatment B step 24 can be a second centrifuge which can be used to separate the pH adjusted mixture P-107 into separate phases based on their specific gravity difference. The recovered oil P-109 can be passed to bulk storage or other processing steps, and the balance of the mixture or post-treatment bottoms P-108 can be returned to the primary feed stream P-100 at, for example, pretreatment B step 22 such that the aqueous and solids phase material can be separated into the aqueous phase P-103 or solid phase P-110. The pH adjusted mixture P-107 can be increased in temperature to increase the specific gravity differences between the various materials in this mixture. In some embodiments the post-treatment B step 24 can be a simple gravity decanter vessel or other separation mechanism comprising hydrophobic and/or hydrophilic filters and/or coalescing filters to enhance oil recovery. In some embodiments, dispersed air bubbles can be used to support coalescing of the freed oil material in the pH adjusted mixture. In some embodiments, depending on the specific characteristics of the light phase mixture P-105, characteristics of the pH adjusted mixture P-107, and the pH adjusted mixture P-107 can be separated by a decanter type clarification vessel or through gravity or forced separation such as with a clarifying centrifuge. In some embodiments, the oil not collected in stream P-109, such as oil still associated with an oil-solid-water suspension or oil present in the adjusted light phase mixture stream P-107, can be mixed with the feed stream P-100 or P-101 and recycled back through the same mechanical separation step 13.

After removal of oil in post-treatment B step 24, the remaining pH adjusted light phase mixture or a portion thereof can be returned to the pretreatment B step 22 where it can be added into the feed stream P-102 to create a combined feed stream and pH treated light phase mixture stream for additional processing through the mechanical separation step 13.

In one embodiment, the feed stillage stream P-100 can be pH adjusted as pretreatment step 22 before the mechanical separation step 13 to decrease the bound oil and increase the free oil in the feed stillage. This technique can, in some embodiments, be effective at increasing the amount of free oil and reducing the amount of oil-solid-water suspension in the light phase mixture stream P-105, but can require a greater amount of pH adjustment reagent to achieve a desired amount of pH change as compared to pH adjustment of stream P-105. In some embodiments, the neutralization of the feed stillage stream, and therefore, the neutralization of the separated aqueous phase stream P-103 can be advantageous.

In some embodiments, optional vapor stream P-106 from post-treatment A step 25 can be combined with stillage P-100 at pretreatment A step 21. Such an addition can be used for reasons similar to the addition of vapor stream P-106 at pretreatment step 12, as described in FIG. 2.

Figure 3B:
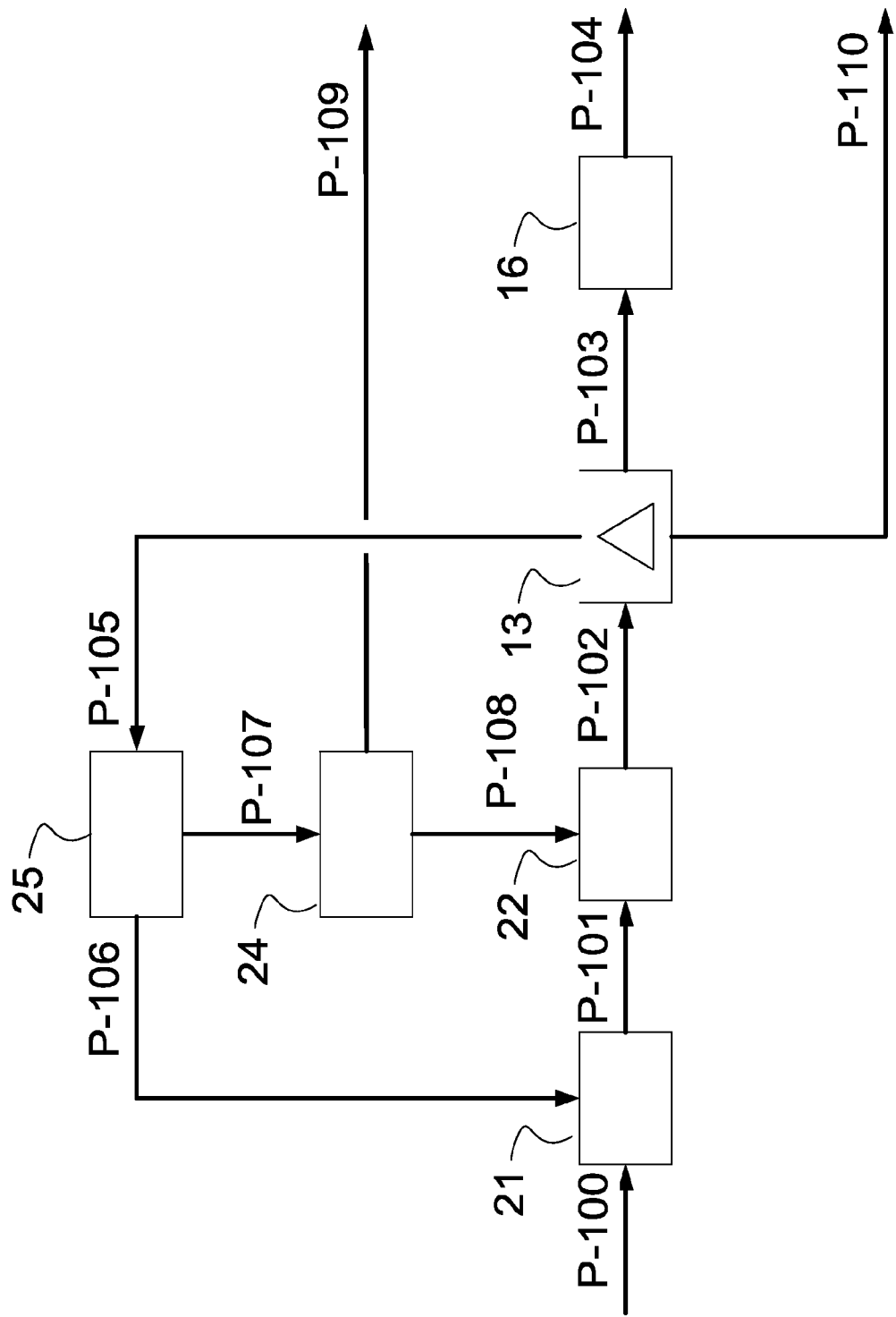
FIG. 3b is an illustration of a process to separate a light phase mixture from stillage with subsequent separation of oil with heat/evaporative treatment and optional separation of aqueous compounds.

Separation of a Light Phase Mixture from Two-Step Pretreated Stillage with Subsequent Oil Recovery with Thermal/Evaporative Treatment and Recycle of Streams In some embodiments, it can be desirable to recycle various streams within the processes described above and perform further processing. In one embodiment, as shown in FIG. 3b, a heating/evaporation treatment step 26 is performed on the light phase material P-105 to facilitate isolation of oil followed by clarification 24 of the post-treated stream P-107 to recover at least a portion of the oil. (The figure reference numbers of FIG. 3b generally correspond to those of FIG. 3a where the same number or indicator is used.)

As shown in FIG. 3b, the light phase mixture P-105 is first passed to the post-treatment step A 25, in which evaporation through the addition of heat and/or the reduction of pressure, causes at least a portion of the moisture present to vaporize into hot water vapor. While not wishing to be bound by theory, it is believed that the evaporation of at least a portion of the water present in the solid matter liberates at least a portion of the oil present in the solid. The temperature and pressure of this step can be maintained to ensure the energy added to the mixture supports the transition of water to the vapor state. In one embodiment, the equipment used for the heating step can be a falling film evaporator, a heat exchanger or a forced circulation heat exchanger. The source of the heating energy can be steam, electricity, combustion gases, high temperature steam condensate, or any other source of heat, with the source of the heat not intended to be limiting. The post-treatment step A 25, which can comprise methods of thermal, evaporative, pH adjustment, and other mechanical and chemical treatments, as well as combinations of methods thereof, supports separation of off-gas stream P-106, as illustrated in FIG. 3a, and hot liquid stream P-107 is passed to a clarification step 24. Here the hot liquid stream is separated into a free oil product stream P-109 and a post-treatment bottoms stream P-108. The off-gas stream P-106 and the bottoms stream P-108 are both passed to the pretreatment step, which has been illustrated as a dilution step 21 and an oil enhancement step 22. In one embodiment, the vaporized off-gas stream is passed to pretreatment A step 21 in which it is mixed with the feed stillage P-100 to support the condensation of the water vapor, the dilution of the stillage stream, and the heating of the stillage stream. The hot diluted stillage P-101 is then introduced into an oil enhancement step 22 in which the oily bottoms P-108 are added and can interact with emulsions and oil-solid-water complexes from feed stream P-100. The bottoms from the clarification step 24 mixed with the hot diluted stillage P-101 results in an enhanced oil stillage stream P-102, which is passed to the mechanical separation process 13. The bottoms of the post-treatment process 15 can be a high oil content mixture of solids and oil with a portion, and in some embodiments a majority, of the colloidal properties or oil-solid-water suspensions modified or destroyed by the post-treatment process. This oily mixture can be dispersed into the hot diluted stillage and can assist the coalescence of the free oil contained in the feed stillage. The addition of the hot bottoms mixture P-108 to the hot diluted stillage can provide additional heat to the stillage stream P-101. The order of the dilution step 21 and the oil enhancement step 22 can be reversed or combined and the order defined is not intended to limit the scope of the innovation. If heating of the feed stream P-101 is not desired the off gas stream P-106 can be added to the aqueous phase P-103 or vented or sent to other uses in the facility. If the oil content of the bottoms stream P-108 is relatively low the bottoms stream can be simply returned to the facility and recycling through the mechanical separation step 13 is avoided.

Figure 4:
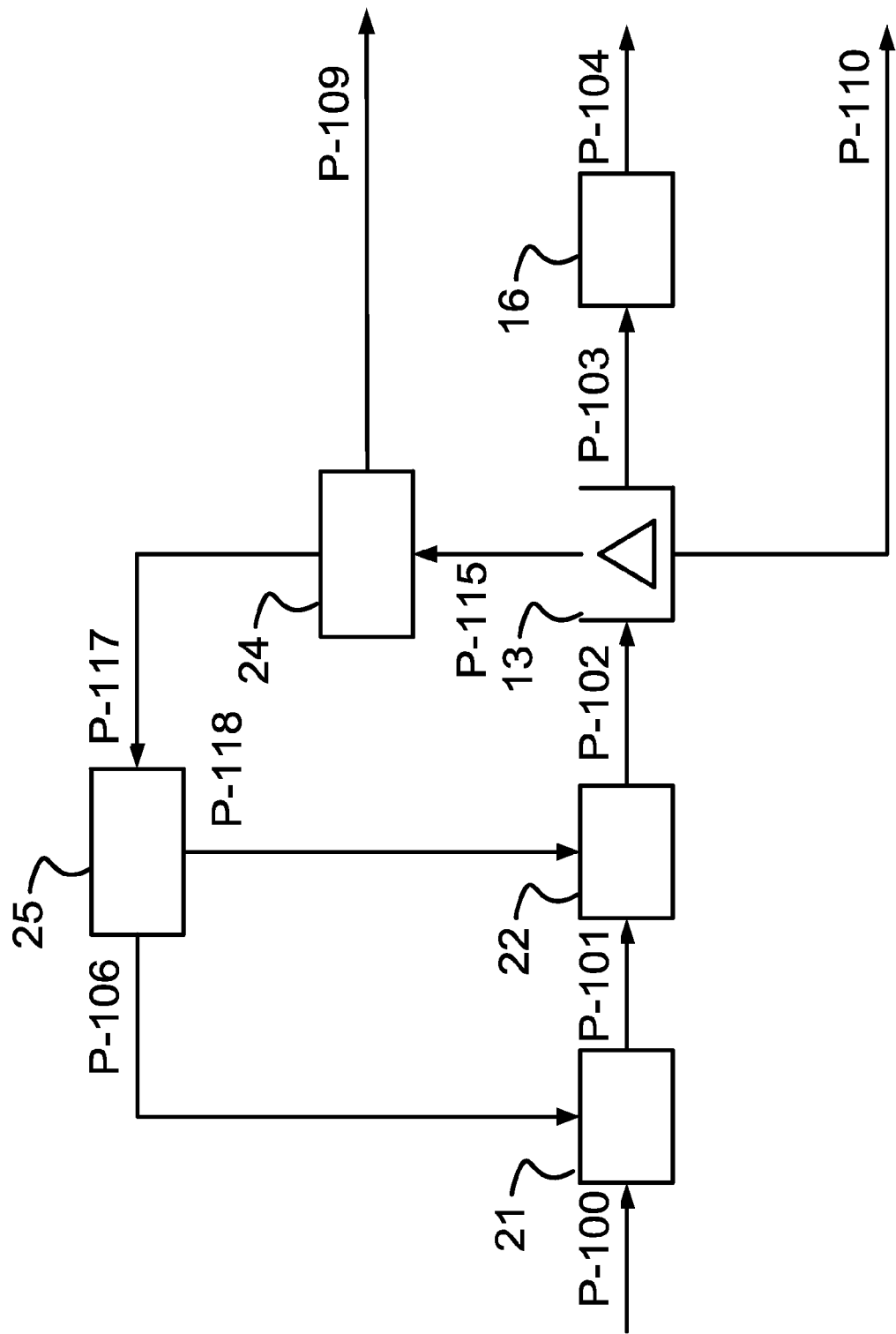
FIG. 4 is an illustration of a process to separate a light phase mixture from stillage with subsequent separation of oil and optional separation of aqueous compounds in which the oil recovery step is upstream of a chemical or thermal/evaporative post treatment.

Separation of a Light Phase Mixture from Stillage with Subsequent Oil Recovery with Post-Treatment after Oil Separation In some embodiments, it can be desirable to order the process steps differently than as described above. In one embodiment, as shown in FIG. 4, clarification or oil recovery step 24 is located upstream of the post-treatment A step 25. (The figure reference numbers of FIG. 4 correspond generally to those of FIG. 3b where the same number or indicator is used.) In one embodiment, as illustrated in FIG. 4, the light phase mixture stream P-115 from mechanical separation process 13 is first passed to the clarification step 24. This clarification step can be a decanter tank or other gravity separation mechanism such as, but not limited to, a centrifuge, as described above. The clarification step 24 can be sized such that the light phase mixture is separated into a low solids content light phase product P-109 and a high solids content stream P-117, which is passed to the post-treatment step P-25. This embodiment can be used, for example, when post-treatment bottoms phase P-118 has a large quantity of oil and oily centrifuged for about five minutes at about 3200 G. Four layers were observed in the centrifuge tubes the topmost layer was free oil. The next layer down was a light phase having a creamy/emulsified appearance and comprising oil-water-solids. The third layer down was a thin aqueous continuous phase with a small amount of other suspended material. The fourth (bottom) layer was a semisolid sludge. The percent volume of the top two layers and the bottom layer were measured. These results were graphed in FIG. 5. These data are also shown in Table 1, below. Two ratios were also calculated from this data. The first ratio is of the volume of the light phase layer to the volume of the free oil layer. The second ratio was total volume of the top two phases (light phase mixture) to the volume of the bottom phase.

TABLE 1

| Sample No. | Solids Layer (bottom), % vol. | Free Oil Layer (top), % vol. | Cream Layer (second layer), % vol. | First Ratio: Cream Layer Volume to Oil Layer Volume | Second Ratio: volume of the top two layers to the solid layer |
|---|---|---|---|---|---|
| 1 | 13.6% | 0.2% | 1.7% | 10.0 | 0.13 |
| 2 | 38.9% | 3.2% | 2.5% | 0.78 | 0.15 |
| 3 | 60.0% | 4.6% | 2.6% | 0.58 | 0.12 |
| 4 | 71.1% | 5.8% | 3.3% | 0.57 | 0.13 |
| 5 | 80.6% | 4.7% | 2.9% | 0.62 | 0.09 | suspensions and it is desired to recycle this material through the mechanical separation step 13 to generate free oil that can be separated easily in the post-treatment B step 24. When desired, this embodiment can be utilized with a chemical post-treatment technique in which a static or other mixer mixes the light phase material and the chemical reagent modifying the properties of the stream and allowing centrifugal force or other techniques to separate free oil from the mixture. In one embodiment, an additional centrifuge can be added to the system after the pH treatment step or the post-treated bottoms P-118 can be recycled back to the initial centrifuge step 22.

Other Features Applicable to Multiple Embodiments

In various embodiments, a heat exchanger can be located to provide heat transfer between the light phase product stream P-109 and the light phase mixture stream P-105. This heat exchange can partially or fully raise the temperature of the light phase mixture stream P-105 prior to the heating step, and it can lower the temperature of the light phase product stream P-109 after the process. Various recuperative heat exchange approaches, including those that utilize an intermediate heat transfer medium and those that do not, are feasible and exclusion of any are not intended to limit the scope of the various embodiments.

EXAMPLES

Example 1

Concentration of Stillage by Evaporation

Thin stillage was collected from the evaporator train of a Type A dry mill ethanol facility. The evaporator train was operated at a temperature of about 160 to about 195° F. The samples were taken at different points in the process, and subjected to different amounts of evaporation prior to collection. Samples were placed in a 25 mL centrifuge tube and When these stillage samples were heated and aged at 90° C. for about 15 minutes to about 180 minutes, the four layers were still present, indicating that heating alone does not completely break the emulsion structure present during this period.

Figure 5:
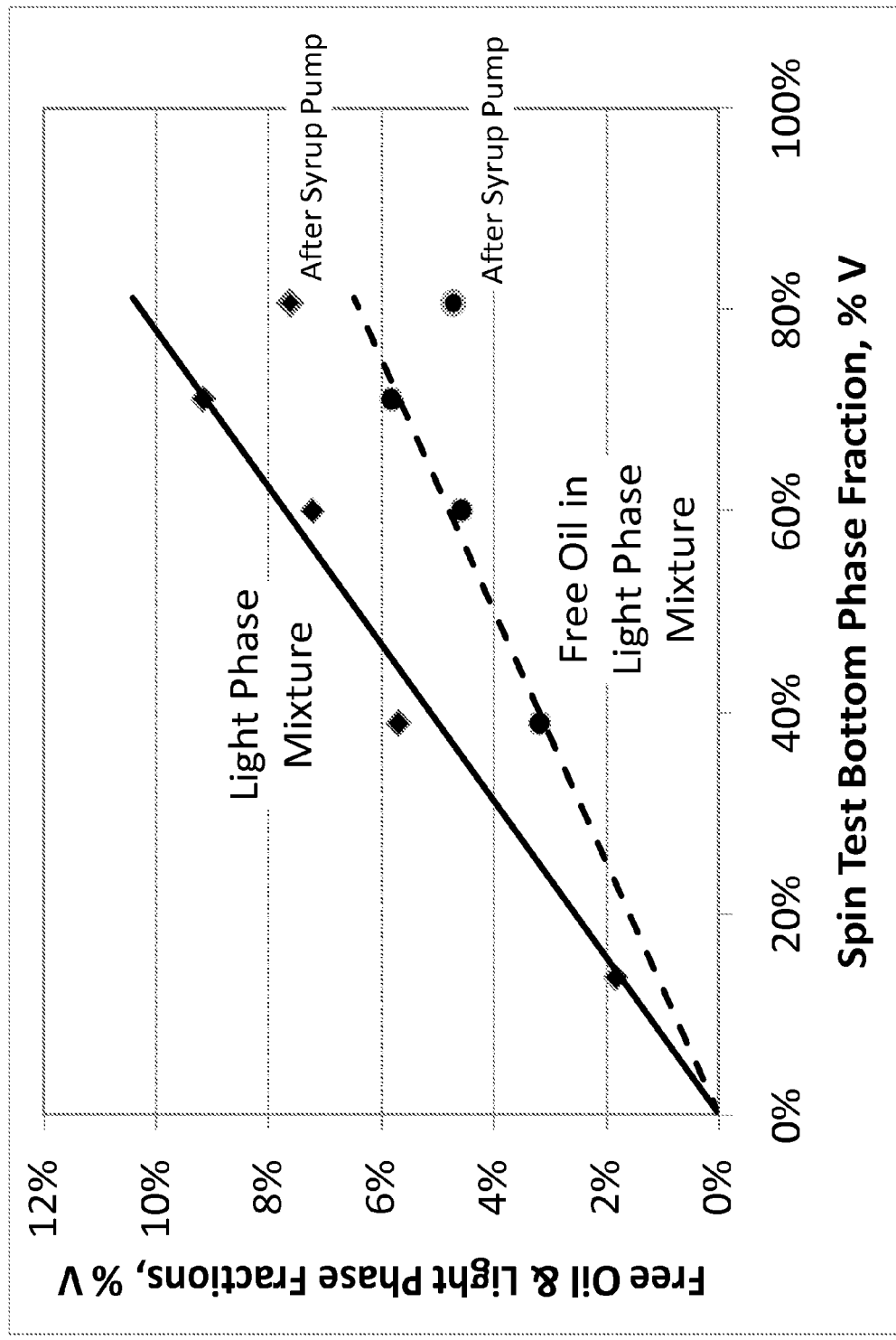
FIG. 5 is a graph showing the linear increase in the concentration of free oil and light phase materials as the thin stillage stream is concentrated in the evaporator train of a commercial ethanol facility.

FIG. 5 illustrates the free oil phase and light phase mixture concentration from four samples along the evaporator train of a typical ethanol plant and a sample from the syrup after the syrup pump. Samples taken from various positions along the evaporator train indicate a linear relationship between the size of the top two layers and the solids layer as the solids concentration increase. The data for Sample Nos. indicates linear increases in the concentration of both the light phase mixture and free oil with the removal of water from the thin stillage as it passes through the evaporator train. (This data is believed to have a +/−10% concentration error band.) The linearity of the graphs and their passage through the origin indicate that the relative size of the top two layers did not change as the concentration of solids increased through the evaporator train. This result is also indicated by the relatively constant value for the first ratio, and indicates that additional evaporation does not cause additional oil to pass from the emulsion phase into the free oil phase during evaporation of thin stillage.

Sample No. 5 was taken after the syrup pump while the other four samples were taken from the evaporator train without being subject to the mixing and shear of the pump. As the solids concentration increases the free oil and the light phase oil-solid suspension can be re-entrained into the solid phase due to the increased formation of colloidal suspensions or high shear pumps that increase the oil-solid suspensions in the complex mixtures. This is indicated by the decrease in observable light phase mixture and free oil concentration after the syrup pump. In addition, over exposure to high temperatures in the evaporator train or driers can degrade the oil through hydrolysis and cross-linking chemical reactions at the unsaturated bonds of the hydrocarbon tails of the triglycerides or free fatty acids.

Example 2

Oil Content Analysis in Example Stillage

Two samples of stillage streams were analyzed and evaluated for oil content, Sample A from a Type A facility and Sample B from a Type B facility. Each sample was taken at a point in the midst of the evaporator train where the process stream had a moisture level of about 82 (wt.) %, with actual values shown in Table 2. In each case, approximately 700 ml of thin stillage from a commercial dry-grind corn ethanol facility was heated to 90° C., divided into 16 individual standard 50 ml tubes, and spun for about 5 minutes at 4000 rpm (3250×g) using an Eppendorf® 5810 centrifuge equipped with an A-4-81 rotor (Eppendorf North America, Hauppauge, N.Y.). The four phases were separated, the light phases were combined and aqueous phases separated from the solids phase samples. The combined phases were re-spun several times to achieve a clean separation of the four various phases: free oil phase, light phase, aqueous phase, and solids phase. The relative mass of each phase is presented in Table 2. The individual phases were collected, weighed, and then analyzed for fat using AOAC Method No. 954.02 (AOAC International, Gaithersburg, Md.).

These results show that additional oil can be recovered from concentrated stillage of ethanol dry grind facilities by solvent extracting the light phase mixture to recover product oil. For Sample A, a 26% increase in oil would be available in Sample A by solvent extracting the oil present in the light phase and combining it with the free oil phase rather than the recovering the free oil phase alone. For Sample B, more than a 1000% increase in oil recovery would be possible because no free oil was present.

TABLE 2

Comparison of Four Separate Phase in Two Stillage Samples

| Spin Test Analysis | Sample A, % mass | Sample B, % mass | Oil Location Sample A, % mass | Oil Location Sample B, % mass |
|---|---|---|---|---|
| Free Oil Phase | 2.9% | 0.0% | 58% | 0% |
| Light Phase | 1.5% | 10.4% | 15% | 66% |
| Aqueous or Heavies Phase | 77.0% | 76.3% | 13% | 29% |
| Solids Phase | 18.6% | 13.3% | 15% | 5% |
| Stillage Moisture, (wt.)% | 82.5% | 82.1% | | |
| Stillage Dry Mass, (wt.)% | 17.5% | 17.9% | | |
| Stillage Oil, % | 4.8% | 5.1% | | |
| Light Phase Mix. Moisture, (wt.)% | 15.3% | 52.0% | | |
| Light Phase Mix. Dry Mass, (wt.)% | 84.7% | 48.0% | | |
| Light Phase Mix. Oil, (wt.)% | 79.6% | 32.7% | | |
| Light Phase Mix. Oil, (wt/)% dry | 94% | 68% | | |

Example 3

Light Phase Post Treatment Test

A sample of light phase material was obtained from a Type A ethanol dry grind facility as follows: 1) the concentrated thin stillage was processed with a disc stack centrifuge to recover oil as the lightest of three outlet streams from the centrifuge; 2) the middle product stream was centrifuged with a decanter centrifuge, and a cream/emulsion phase was recovered and collected. Approximately 1000 ml of the collected material was fed at a flow rate of 10 ml/minute (feed material) through a heat exchanger tube (¼ inch O.D. stainless tubing, 10 ft. long, bent into a coil) placed in a hot oil bath. The outlet of the coil discharged into an open beaker with no valve or backpressure device present, with samples collected at this point. The temperature of the oil bath was adjusted from 115° C. to 150° C. and samples were collected with the initial 200 ml of processed material discarded. This technique allowed evaporation of at least a portion of the water present during processing, and, at least in some cases, condensation of at least a portion of the water vapor back into the collected sample, either prior to or after discharge from the coil. This test was very preliminary but illustrated that 74 to 84% of the volume of the light phase material can be recovered as free oil and that an increasing amount of recovered free oil was achieved as the temperature/extent of evaporation was increased. Also, the oil recovered by this processing step is oil that was not recovered by centrifugation of concentrated thin stillage.

TABLE 3

Experimental Results of Initial Light Phase Post Treatment

| | Approx. Temp of Oil Bath while processing 200 ml | | | |
|---|---|---|---|---|
| | 115° C. | ~135° C. | ~145° C. | ~155° C. |
| Free Oil Phase, % vol | 74% | 78% | 80% | 84% |
| Light Phase, % vol | 26% | 6% | 3% | 3% |
| Aqueous Phase, % vol | 0% | 6% | 8% | 4% |
| Solid Phase, % vol | 0% | 11% | 9% | 9% |

Example 4

Light Phase Post Treatment Experiment

A sample of light phase material, obtained in the same manner as the sample in Example 3, was passed through a small scale, single pass heat exchanger contained in a hot oil bath at temperatures ranging from 105° C. and 170° C. (220° F. to 340° F.) to evaluate effect various degrees of evaporation. Seven tests at flow rates ranging from 5 to 15 ml/min such that the mixture exited between 100° C. to 130° C. (210° F. to 270° F.) were made with no back pressure applied to maintain the light phase mixture at or near ambient pressure to allow the evaporation of water from the mixture during processing. Two tests were conducted where the mixture was maintained at 1.5 atm gauge (22 psig) pressure and between 110° C. to 130° C. (230° F. to 260° F.) at the exit.

Figure 6A:
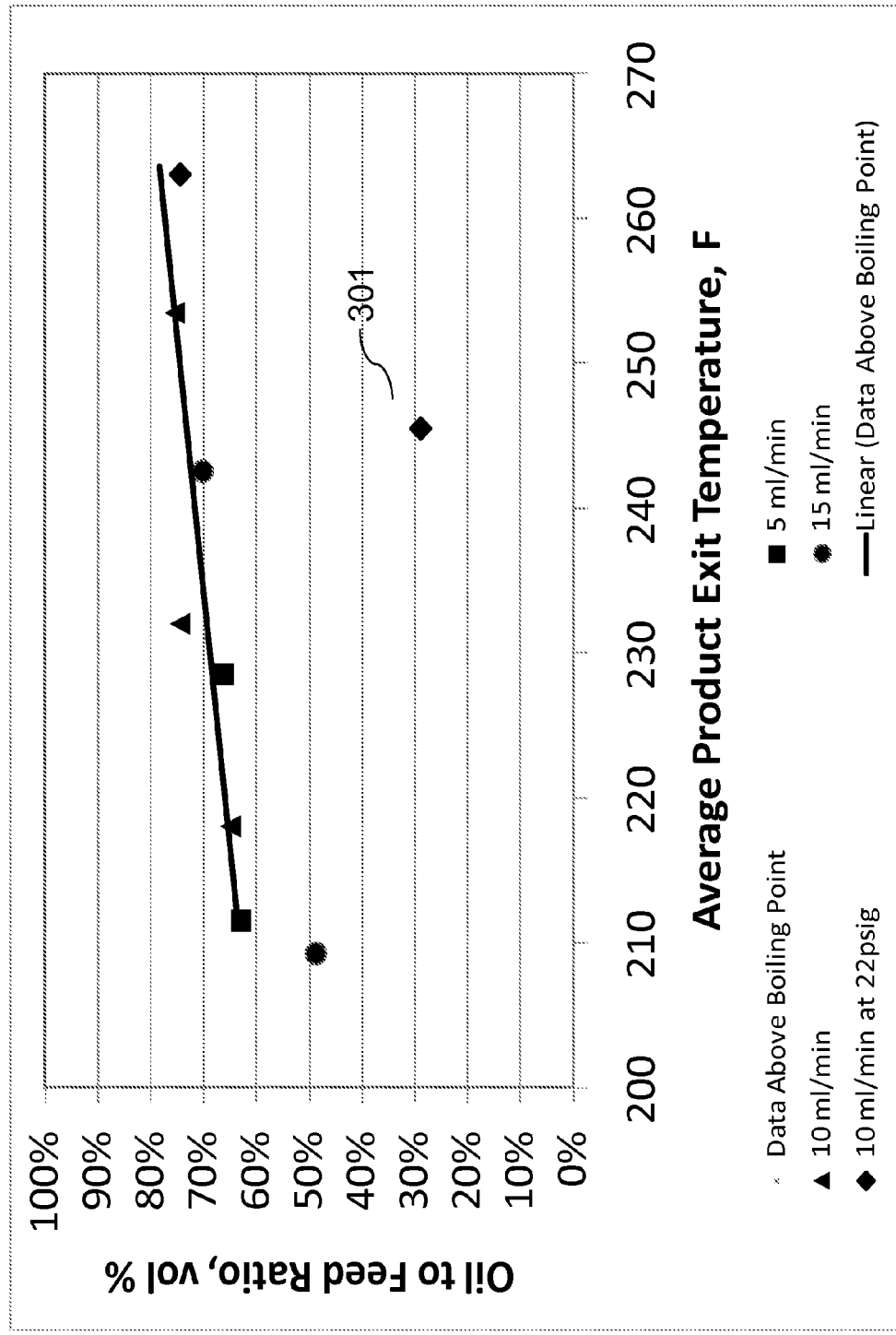
FIG. 6a is a graph of the volume fraction of free oil in the light phase mixture as a function of post treatment temperature.
Figure 6B:
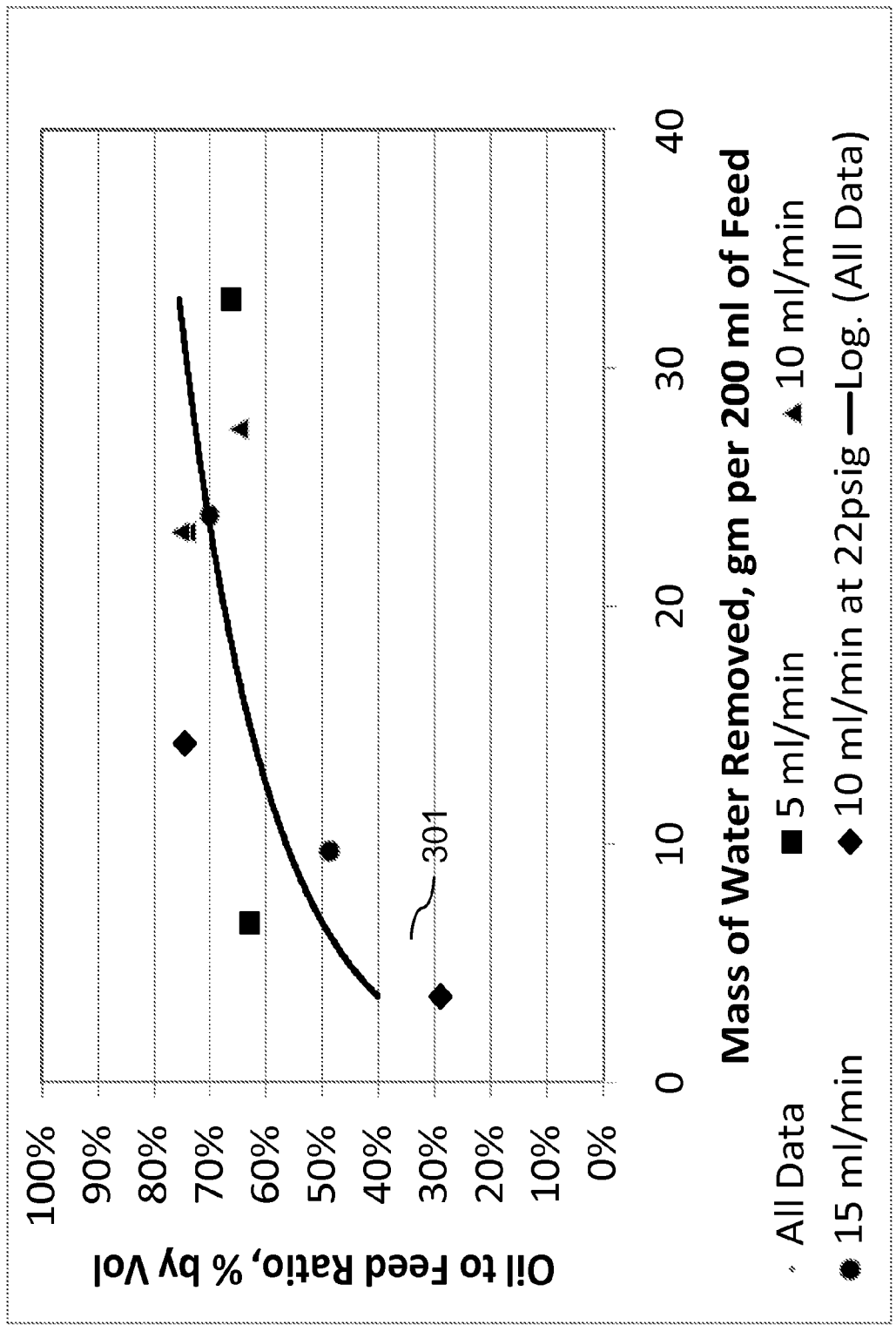
FIG. 6b is a graph of the volume fraction of free oil in the light phase mixture as a function of the amount of water removed from the light phase material.

FIG. 6a illustrates a linear effect of oil recovery as a function of temperature for seven data points. The data point 301 had sufficient back pressure to prevent evaporation during processing (boiling point of water at 36.7 psia, or 22 psig is 262° F.) Likewise, the lowest temperature sample (and second lowest free oil to feed ratio), processed to 100° C., had sufficient dissolved compounds present in solution to raise the boiling point and suppress evaporation, leading to a smaller improvement in the recovery of free oil. The results of these tests are presented in FIGS. 6a and 6b, which illustrate the final product oil to feed volume ratio as a function of the average exit temperature (see FIG. 6a) and the mass of water evaporated and condensed downstream (see FIG. 6b). The same data, when plotted as a function of the mass of water removed indicates that the amount of water removed is important for oil recovery. This effect is most clearly demonstrated by data point 301, which received high-temperature treatment, but low evaporation, and demonstrated relatively low oil recovery. However, elevated temperature is important as well, as indicated by the performance of the lowest temperature sample which demonstrated improved oil recovery than the untreated material, but lower oil recovery than a higher temperature processed sample with similar evaporation.

The accuracy of these preliminary tests is approximately +/−10% points. The maximum amount of oil in the feed mixture is approximately 75-80% (vol.). The lowest recovery was at the cold exit temperature and elevated pressure, which indicates that the removal of water from the solids in the suspension can have a stronger effect on oil recovery than processing temperature, but processing temperature is also important.

Example 5

Post Treatment with pH solution

Three samples of stillage were used to assess the effect of a pH adjustment in a post-treatment step. The samples tested were Sample B from Example 2 (stillage), light phase from Example 2 Sample A, and light phase from Example 2 Sample B.

The light phase mixtures were prepared by transferring concentrated stillage into 1 liter capped bottles and holding in a water bath set at 95 C for one hour. The samples were then poured into four 50 mL centrifuge bottles (45 mL per bottle) and spun for 30 minutes at 4000 rpm (3250×g) using an Eppendorf 5810 centrifuge equipped with an A-4-81 rotor. Sample B had no free oil phase present; Light Phase A had a free oil phase; Light Phase B had no free oil phase present. The light phase mixtures, Light Phase A with the free oil, and the other two samples without free oil, were collected and transferred into separate containers.

Each of the three test samples was titrated with 5% NaOH solution using 50 gm of test sample. The results of the titration curves are shown in FIG. 7. These titration curves each have a change in slope/inflection point/discontinuity in the vicinity of the pH where maximum oil recovery occurred.

Figure 9:
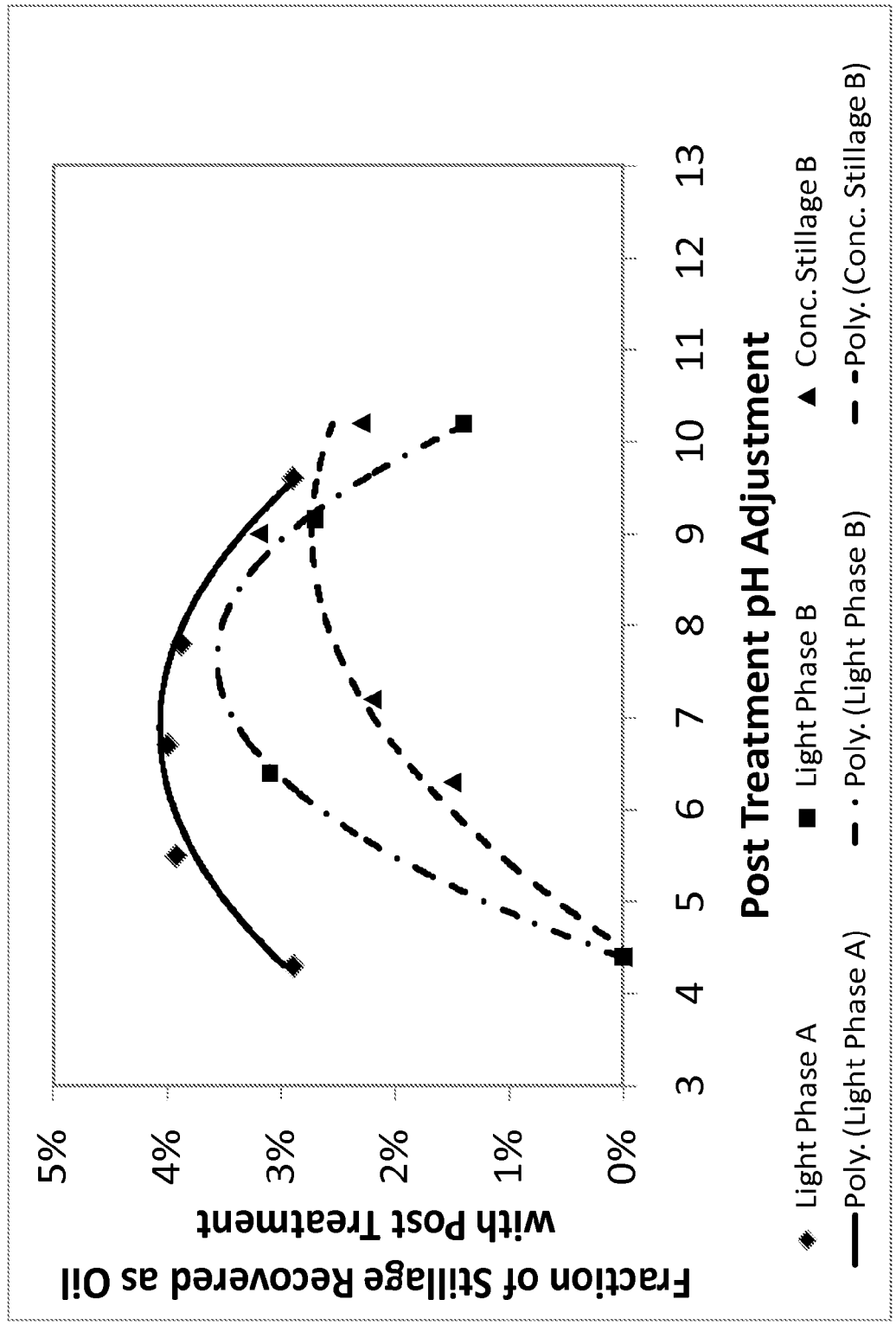
FIG. 9 is a graph of the volume fraction of free oil present after chemical treatment as a function of pH.
Figure 11:
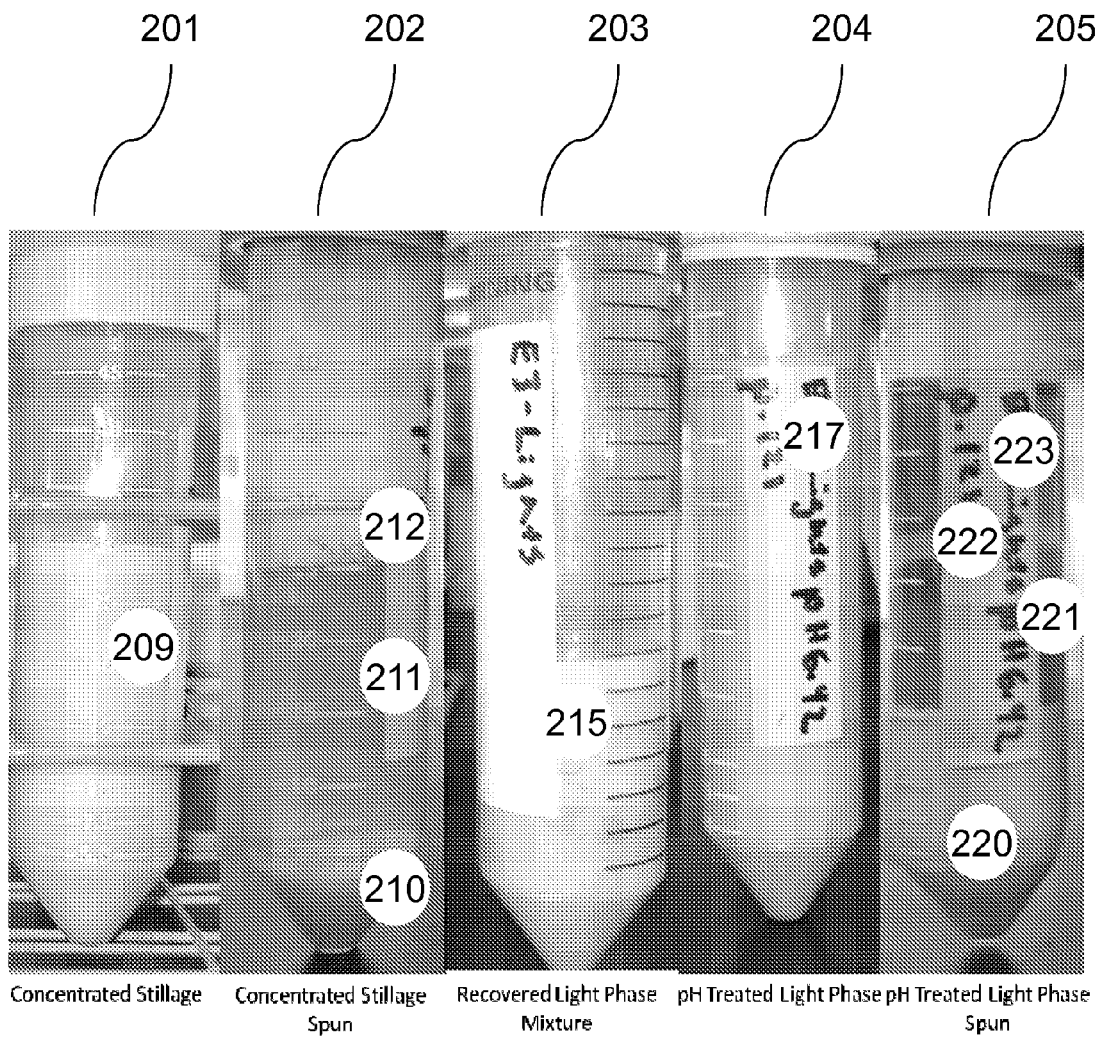
FIG. 11 is a picture showing the different layers for the tabulated data of FIG. 8.

FIG. 8 tabulates the effects of pH post treatment on the stability of the Sample B from Example 2. (All percents in FIG. 8 are by volume.) Pictures of the samples and treatments described in FIG. 8 are also provided in FIG. 11. Five test tubes are described during various stages of the procedure. The concentrated stillage 209 is contained in the first test tube 201. This stillage 209 is centrifuged to separate out the various phases of the stillage as described for the second test tube 202. Three phases are represented—the first solids phase, the first aqueous phase, and the first light phase. No first free oil phase was present, as indicated in Table 2. The light phase material from several centrifuged aliquots was collected in the third test tube 203. This material was pH adjusted to 6.4 to generate a pH adjusted light phase and placed in the fourth test tube 204. This material was then centrifuged both cold and warm to promote the separation of the various phases as described for the fifth test tube 205, which clearly indicates a four phase separation—second free oil phase, second light phase material, a second aqueous phase material, and a second solid phase material. This method was used on several test samples of the three target materials previously identified as Sample B (Con Stillage B), Light Phase of Sample B (Lights B), and Light Phase of Sample A (Lights A), as described in Example 2. The approximate oil recovery by weight with the pH post treatment method was measured at a range of pH adjustments from above about 6 to less than about 11 to assess oil recovery. Data for unadjusted samples without post treatment are represented by the base stillage with a pH of about 4 to 4.5. The results for the amount of oil recovered as a function of pH are illustrated in FIG. 9 showing both the data and an Excel® (Microsoft Corp., Redmond, Wash.) polynomial fit for each data set. This graph shows a peak in the amount of oil recovered that corresponds to a change in the slope/inflection point/discontinuity in the titration curve for each of the samples tested. For these samples, the peak occurred over a range of about 6 to about 9. In some embodiments, the operating ranges for pH adjustment is between about 6 and about 11. This data also indicates that the improved results can be achieved with light phase mixture at a lower pH (about 5 to about 9, about 5.5 to about 8.5, about 6 to about 8, and in some cases about 6 to about 7 or about 7 to about 8) than for stillage or concentrated stillage or syrup (about 6 to about 11, or about 7 to about 10.5, or about 8 to about 10, or about 8.5 to about 9.5), but frequently an overall range of about 6 to about 11 or about 7 to about 10 can be used for both streams, or a range described for one stream (light phase mixture or a form of stillage) can be utilized for the other stream and achieve acceptable results.

Example 6

High Value Compound Identification

Figure 10:
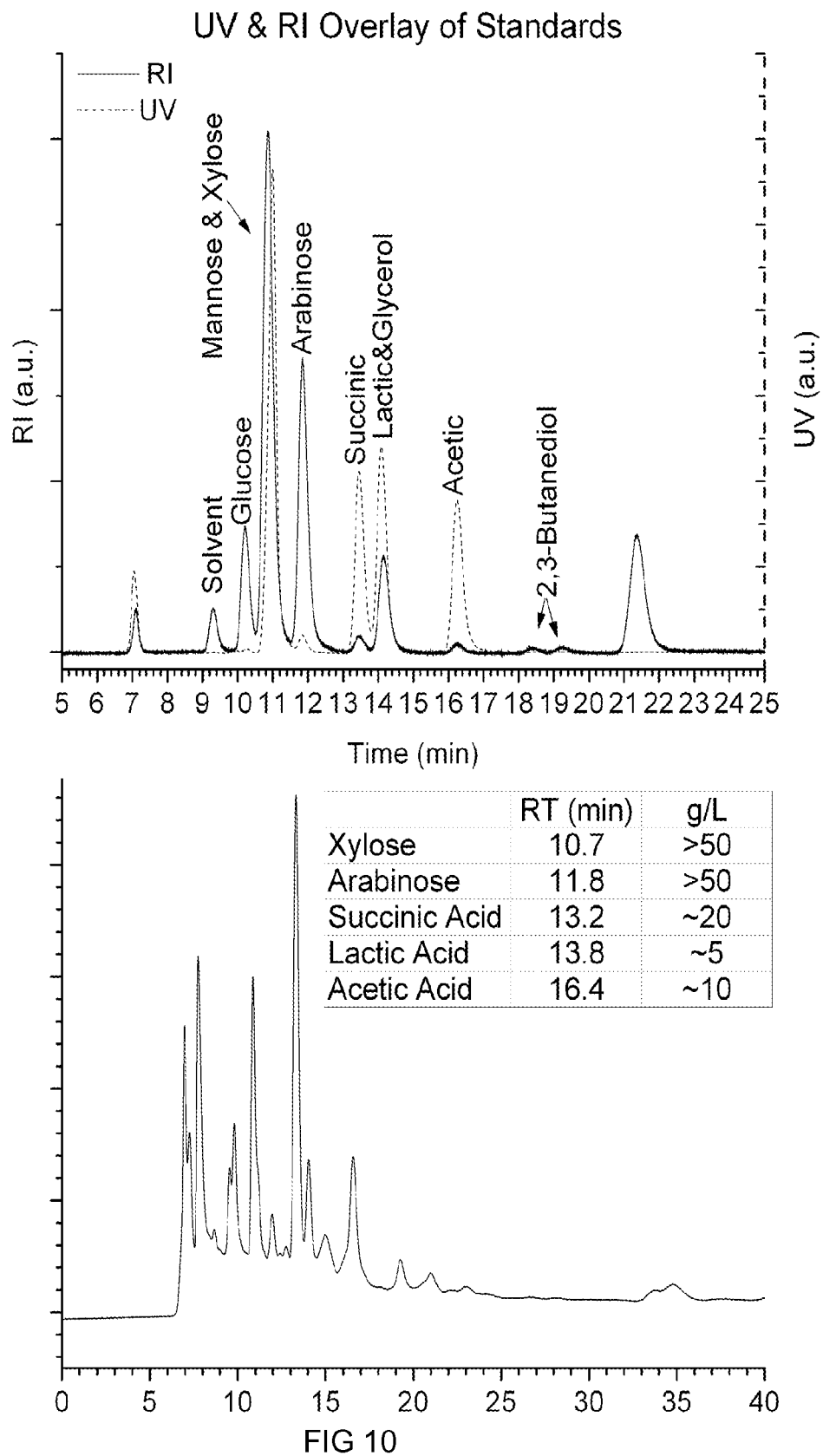
FIG. 10 is a chromatogram showing compounds which can be recovered from the aqueous phase stream.

FIG. 10 shows the HPLC (high performance/pressure liquid chromatography) data obtained from a filtered syrup sample taken from an ethanol plant. The Perkin Elmer HPLC was equipped with an automatic injector and UV/RI detectors. The UV wavelength was set to 205 nm. An ion exclusion column held at 60 C was used to perform the separation. The eluent was 0.01 M HCl solution and the injection volume was 5 µL with an eluent flow of 0.65 ml/min. The resulting peaks were identified against the retention times of the standards as shown in FIG. 10. The areas under the curve were used to calculate the concentrations against the known concentrations of the standards.

Example 7

Stillage Generated from Pretreated Biomass Particles

The stillage sample use in this example was generated from pretreated biomass particles having a relatively smaller particle size, e.g., biomass particles milled using a colloidal mill. A stillage sample was taken from the evaporator train of an operating commercial ethanol facility. Approximately 2.8 kg of stillage was heated to 90° C., divided into 400 gm sample vessels and spun to separate the free oil, light phase mixture 1, and light phase mixture 2 from the balance of the stillage solids and aqueous layers. The various layers were removed and placed in separate containers for analysis to determine the mass percent of the stillage. Samples of the light phase mixture 1 and light phase mixture 2 was then treated with the chemical/pH adjustment method or the heating/evaporating method to release additional free oil from the emulsion of the mixtures. After centrifuging of the treated samples the relative mass of oil from each layer was then measured to determine the oil mass percent of the original stillage and the total oil was determined by summing the mass percentage of each phase.

The light phase mixtures of the stillage sample that was chemically treated by adjusting the pH of the mixture to approximately a level of 7.0. The light phase mixtures of the stillage sample that was treated by heating to evaporate the moisture content of the emulsion was heated to approximately 115° C. A centrifugation was used on both samples to separate the oil from the remaining material and determine the relative mass of free oil in each layer. In comparison, a small sample of the each layer was spun at high speed at approximately 14,000 rpm, much greater than normal industrial process equipment can achieve, to generate a baseline untreated comparison. The results are summarized in Table 4.

TABLE 4

|  | Mass, % wt of the stillage | Oil, % wt of the light phase mixture | Oil, % wt of the stillage | Total Oil, % wt of the stillage |
|---|---|---|---|---|
| pH treatment |  |  |  | 5.3 |
| Free Oil | 0.4 | 100% | 0.4 |  |
| Light phase mixture 1 | 4.8 | 84.4% | 4.1 |  |
| Light phase mixture 2 | 2.8 | 27.7% | 0.8 |  |
| Heating/centrifugation |  |  |  | 3.6 |
| Free Oil | 0.4 | 100% | 0.4 |  |
| Light phase mixture 1 | 4.8 | 64.3% | 3.1 |  |
| Light phase mixture 2 | 2.8 | 1.7% | 0.05 |  |
| Spin test ("Untreated") |  |  |  | 4.6-5.2 |
| Free Oil | 0.6 | 100% | 0.6 |  |
| Light phase mixture 1 | 5.8 | 60-70.3% | 4.1 |  |
| Light phase mixture 2 | 6.1 | 7.5% | 0.5 |  |

Example 8

Stillage Generated from Pretreated Biomass Particles

Two stillage samples were used in this example. The "first stillage sample" was generated from biomass particles having a relatively larger particle size, e.g., biomass particles that have not been milled using a colloidal mill. The "second stillage sample" was generated from pretreated biomass particles having a relatively smaller particle size, e.g., biomass particles milled using a colloidal mill. Both samples were taken from the same commercially operating ethanol facility, but the first stillage sample was taken before process modifications which created the relatively smaller particle size of "second stillage sample." For each sample the stillage was placed in four 50 ml centrifuge tubes, which were capped and heated to approximately 90 C, and then spun for 5 minutes at 4000 rpm (3250×g) using an Eppendorf® 5810 centrifuge equipped with an A-4-81 rotor (Eppendorf North America, Hauppauge, N.Y.). The independent layers were separated and combined, and the relative mass of each layer was measured and compared. After centrifuging the samples the first stillage sample had free oil, light phase mixture 1, aqueous phase, and solid phase layers, while the second stillage sample also showed a defined light phase mixture 2 layer. These samples were not sufficient in volume to conduct actual treatment of the light phase mixtures.

Figure 12:
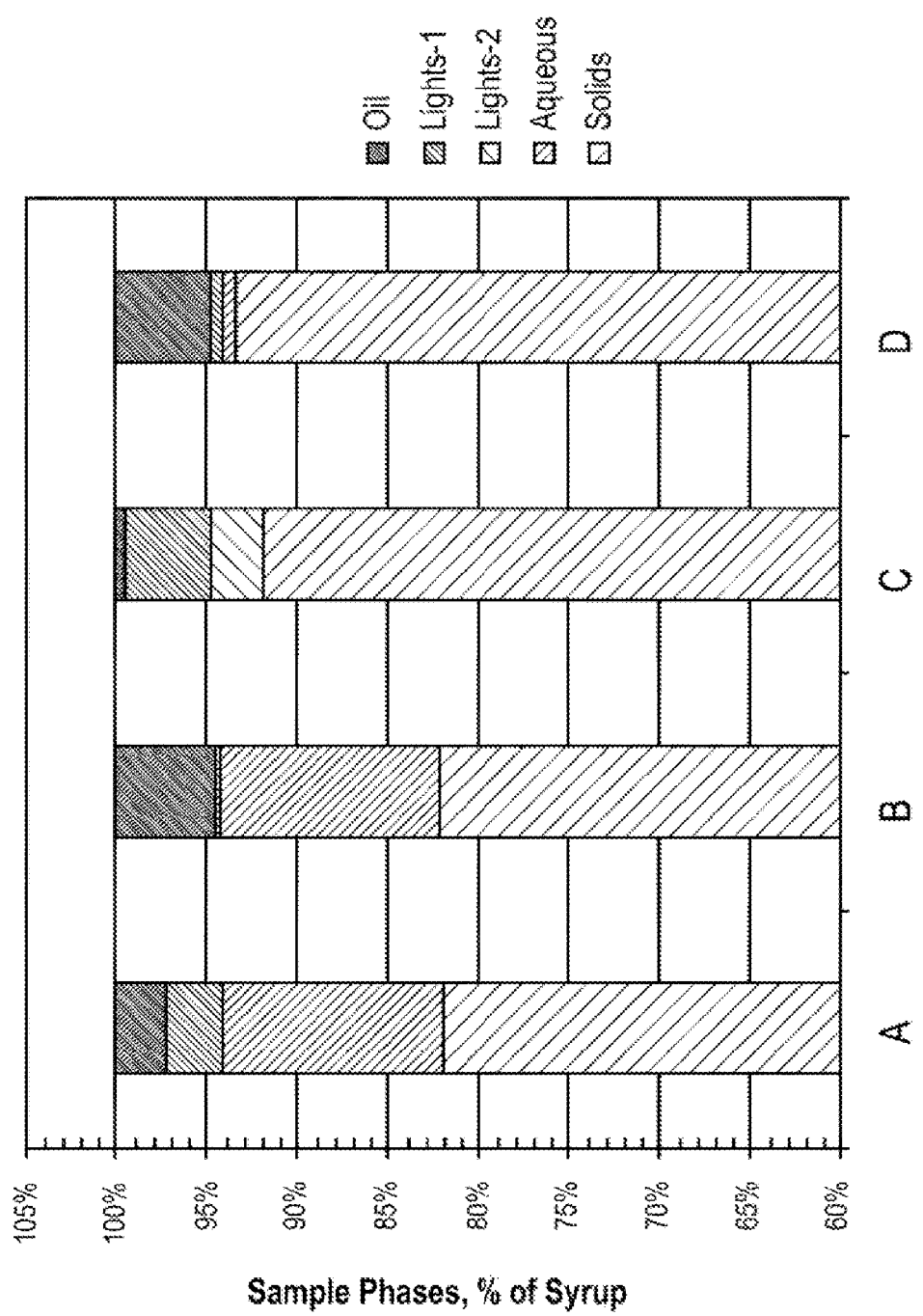
FIG. 12 is a comparison of free oil content and oil recoverable from A) "First stillage sample"; B) "First stillage sample" with chemical treatment; C) "Second stillage sample"; and D) "Second stillage sample" with chemical treatment.

The first stillage sample had about 2.7% wt free oil and about 3.3% wt light phase material. The second stillage sample had about 0.6% wt free oil. There were two different layers of light phases in the second stillage sample: (1) a darker emulsion layer with higher oil content (Light-1 phase); and (2) a lighter emulsion layer with lower oil content (Light-2 Phase). These results are presented in Table 5 for both the mass and volume ratios. Based on the previous results of Example 7, estimates were made based on the expected free oil content of the various light phase mixtures after chemical treatment. The light phase mixture of the second stillage sample yielded 5.3% oil if it were treated chemically (FIG. 12).

TABLE 5

|  | Oil | Light-1 | Light-2 | Aqueous | Solids |
|---|---|---|---|---|---|
| Mass, % of the stillage | | | | | |
| "First stillage sample" | 2.7 | 3.3 |  | 12.1 | 81.9 |
| "Second stillage sample" | 0.64 | 5.8 | 6.1 | 1.8 | 85.7 |
| Volume, % of the stillage | | | | | |
| "First stillage sample" | 3.6 | 4.3 |  | 12.5 | 79.7 |
| "Second stillage sample" | 0.84 | 7.0 | 6.3 | 2.0 | 83.9 |

Example 9

Stillage Generated from Pretreated Biomass Particles

Two stillage samples were used in this example. The "first stillage sample" was generated from biomass particles having a relatively larger particle size, e.g., biomass particles that have not been milled using a colloidal mill. The "second stillage sample" was generated from pretreated biomass particles having a relatively smaller particle size, e.g., biomass particles milled using a colloidal mill. Both samples were taken from the same commercially operating ethanol facility, but the first stillage sample was taken before process modifications which created the relatively smaller particle size of "second stillage sample." For each sample the stillage was placed in four 50 ml centrifuge tubes, which were capped and heated to approximately 90 C, and then spun for 5 minutes at 4000 rpm (3250×g) using an Eppendorf® 5810 centrifuge equipped with an A-4-81 rotor (Eppendorf North America, Hauppauge, N.Y.). The independent layers were separated and combined, and the relative mass of each layer was measured and compared. After centrifuging the samples the first stillage sample had free oil, light phase mixture 1, aqueous phase, and solid phase layers, while the second stillage sample also showed a defined light phase mixture 2 layer. These samples were not sufficient in volume to conduct actual treatment of the light phase mixtures.

The "Second Stillage Sample":

The pH of the second stillage sample was measured at 4.3, prior to treatment. Additional volumes of the second stillage sample material was obtained and was used to fill four 50 ml lab centrifuge tubes to 45 ml. Capped tubes were heated for two hours at approximately 90° C. Tubes were then centrifuged in lab centrifuge for 5 minutes at 4000 rpm to separate the free oil and light phase mixtures.

Small amount of free oil was observed to be present on top. There were two different layers of light phases: (1) a darker emulsion layer with higher oil content (Light-1 phase); and (2) a lighter emulsion layer with lower oil content (Light-2 Phase). There were also a very small aqueous phase layer and a large fraction of solids layer. Various layers were removed and measured.

The oil contents of the Light-1 phase, Light-2 phase, and the whole second stillage sample were estimated. Light-1 Phase was heated and centrifuged at 4000 rpm for 5 minutes. Approximately 75% wt of material is oil. Light-2 Phase was spun at 14000 rpm for 5 minutes. Approximately 7.5% wt of material is oil. The whole second stillage sample was spun at 14000 rpm for 5 minutes. Approximately 6.6% wt of material is oil.

Figure 13:
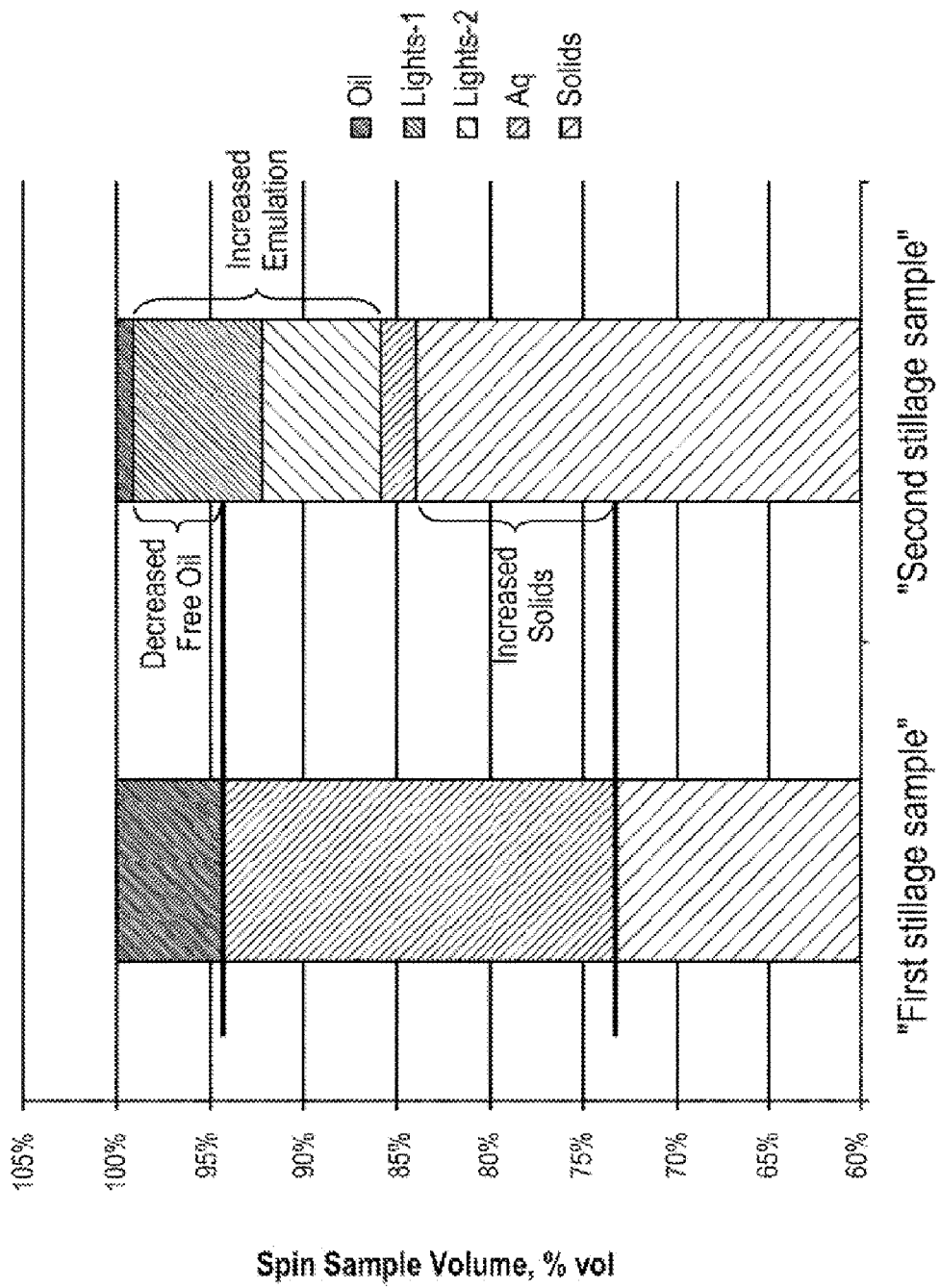
FIG. 13 shows a comparison between the first stillage sample and the second stillage sample.

Results:

FIG. 13 provides a comparison of the stillage characteristics showing the results of lab spin tests. The spin tests separate the stillage into the following multiple layers based on specific gravity—free oil, oil emulsion, aqueous phase and solids phase. As shown in FIG. 13, the second stillage sample had a decreased volume of free oil, an additional emulsion layer, and an increased volume of solids phase, as compared to the first stillage sample. Approximately 5% of the first stillage is free oil. Less than 1% of the second stillage is free oil.

Figure 14:
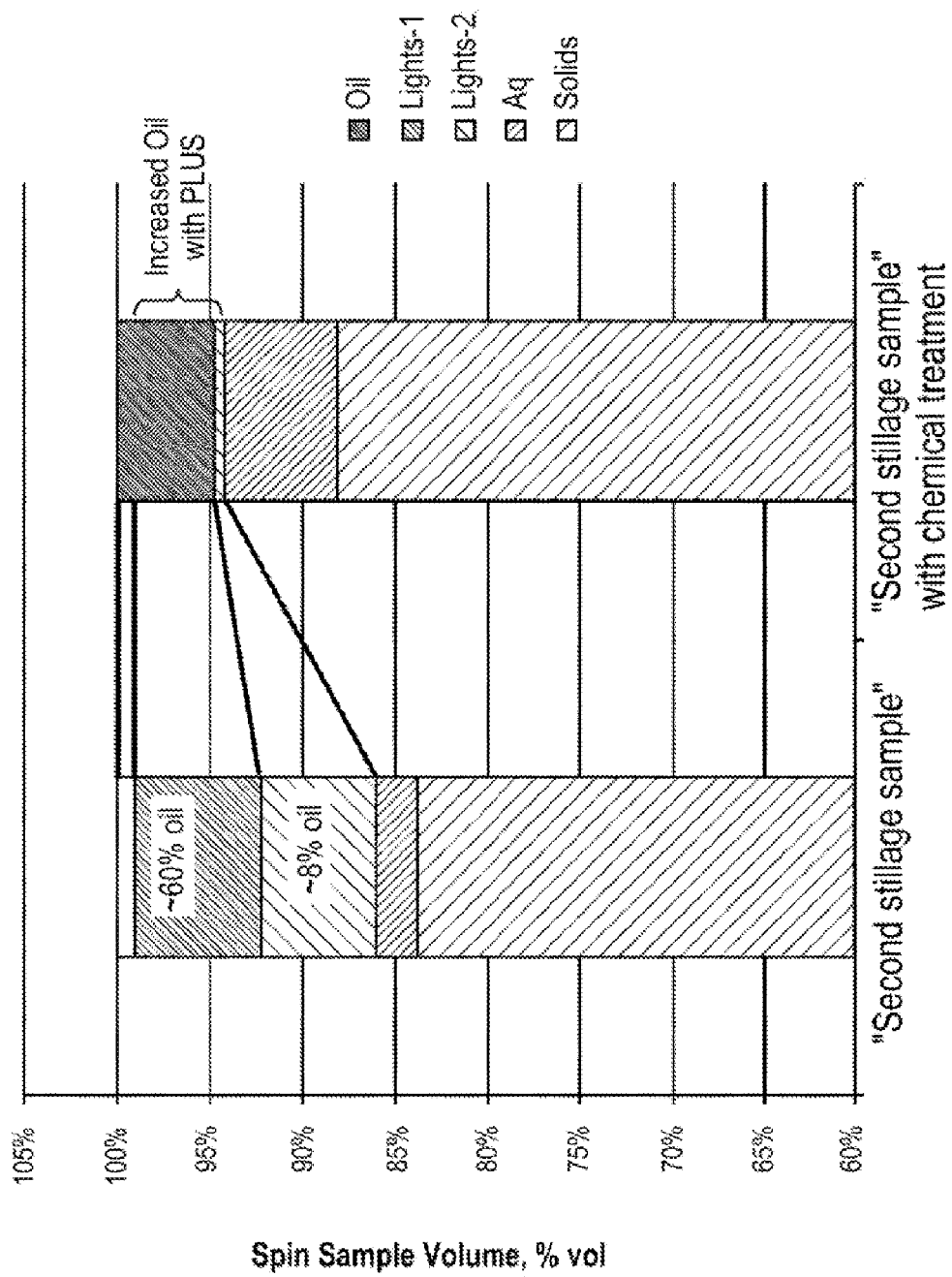
FIG. 14 shows the oil content of the emulsion layer in the second stillage sample with or without chemical treatment.

The second stillage sample had a significant emulsion layer that was not present in the first stillage sample. Approximately 14% of the second sample is oil/emulsion, with two relatively distinct emulsion layers, labeled as "Lights-1" and "Lights-2." Typically, only a single Lights-1 layer is observed in spin tests, with about 50 to 65% oil content. As shown in FIG. 14, the Lights-1 layer from the second stillage had about 60% oil content. An analysis of the Lights-2 layer using a high intensity centrifuge showed less than 10% oil content and approximately equal amounts of solids and aqueous phases. This data indicates that the most of the free oil is entrained in the emulsion layers.

The second stillage sample was centrifuged to extract both the free oil and the emulsion layers as a light phase mixture. This light phase mixture was then chemically treated to break the emulsions, e.g., by adjusting the pH of the mixture to approximately 7. Finally, oil was extracted from the chemically treated light phase mixture. Chemical treatment of the light phase mixture of the second stillage yielded in a level of recoverable oil up to 5%, which is comparable to the level observed in the first stillage sample.

As summarizes in Table 6, the second stillage sample had approximately 10% points greater solids layer than the first stillage sample (FIG. 13). When the emulsion layers are broken down into free oil, aqueous phase, and solids phase materials as shown in FIG. 14, the resulting solids layer was almost 15% points greater. Finally, the second stillage sample had increased emulsion and solids layers, and substantially reduced free aqueous phase layer. The wt % of aqueous layer was reduced from 21% in the first stillage sample to approximately 2% in the second stillage sample. Assuming the dry mass fraction of both samples is similar, the aqueous phase has been entrained in the solids layer with its finer particle sizes resulting in a lower density layer.

TABLE 6

|  | Oil (%) | "Lights-1" (%) | "Lights-2" (%) | Aqueous (%) | Solids (%) | Recoverable Oil, (%) |
| --- | --- | --- | --- | --- | --- | --- |
| Percentage by weight | | | | | | |
| "First stillage sample" | 5.0 | 0.0 | 0.0 | 21.3 | 74.8 | 5.0 |
| "Second stillage sample" | 0.6 | 5.8 | 6.1 | 1.8 | 85.7 | 0.6 |
| "Second stillage sample," chemically treated | 0.6 | 3.5 | 0.5 | 5.7 | 89.7 | 4.6 |
| Percentage by volume | | | | | | |
| "First stillage sample" | 5.6 | 0.0 | 0.0 | 21.1 | 73.3 | 5.6 |
| "Second stillage sample" | 0.8 | 7.0 | 6.3 | 2.0 | 83.9 | 0.8 |
| "Second stillage sample," chemically treated | 0.8 | 4.4 | 0.5 | 6.2 | 88.1 | 5.7 |

Conclusion:

The total oil content of the first stillage sample and the second stillage sample were about the same, i.e., about 5.6% by volume or about 5% by weight. Entrainment of about 80% of the free oil in an emulsion layer was observed in the second stillage sample due to the smaller particle size and increased number of small particles. Chemical treatment was effective to recover the entrained oil.

All references cited herein, including but not limited to published and unpublished applications, patents, and literature references are incorporated herein by reference in their entirety and are hereby made a part of this specification. To the extent publications and patents or patent applications incorporated by reference contradict the disclosure contained in the specification, the specification is intended to supersede and/or take precedence over any such contradictory material.

The term "comprising" as used herein is synonymous with "including," "containing," or "characterized by," and is inclusive or open-ended and does not exclude additional, unrecited elements or method steps.

All numbers expressing quantities of ingredients, reaction conditions, and so forth used in the specification are to be understood as being modified in all instances by the term "about." Accordingly, unless indicated to the contrary, the numerical parameters set forth herein are approximations that may vary depending upon the desired properties sought to be obtained. At the very least, and not as an attempt to limit the application of the doctrine of equivalents to the scope of any claims in any application claiming priority to the present application, each numerical parameter should be construed in light of the number of significant digits and ordinary rounding approaches.

Specific gravity measurements are reported at and referenced to 25° C., unless stated otherwise or the context indicates otherwise.

Percentages are weight percentages unless stated otherwise or the context indicates otherwise.

The above description discloses several methods and materials of the present invention. This invention is susceptible to modifications in the methods and materials, as well as alterations in the fabrication methods and equipment. Such modifications will become apparent to those skilled in the art from a consideration of this disclosure or practice of the invention disclosed herein. Consequently, it is not intended that this invention be limited to the specific embodiments disclosed herein, but that it cover all modifications and alternatives coming within the true scope and spirit of the invention.

What is claimed is:

1. A method of recovering desired co-products from post fermentation stillage streams, comprising:

a) milling a biomass/water mixture to produce a relatively uniform particle size of less than 1600 microns;

b) fermenting the biomass mixture to generate a primary product and a post fermentation stillage stream;

c) mechanically separating the stillage stream into streams comprising a light phase material and an aqueous phase material, wherein the light phase material comprises at least 5% moisture by weight and greater than 50% lipid materials; and d) recovering products from the separated streams.

2. A method of claim 1, wherein the recovering products comprises separation of essentially lipid material from the light phase material.

3. A method of claim 1, wherein the stillage stream is thin stillage, concentrated thin stillage, or syrup.

4. A method of claim 1, wherein the aqueous phase material is essentially stillage with reduced oil/lipid content.

5. A method of claim 1, wherein the recovering products comprises recovery of other desired products.

6. A method of claim 5, wherein the other desired products comprise organic acids, glycerin, sugars, proteins, amino acids, soluble/insoluble fibers, polysaccharides, oligosaccharides, peptides, polypeptides, betaines, carbohydrates, vitamins, enzymes, fatty acids, succinic acid, lactic acid, acetic acid, citric acid, fumeric acid, folic acid, and/or phytic acid.

7. A method of claim 1, wherein the milling is performed using a colloidal mill.

8. A method of claim 1, wherein at least 95% of the particles have a particle size from about 100 microns to about 800 microns.

9. A method of claim 8, wherein the biomass is grains and the primary product is ethanol.

10. A method of claim 9, wherein the mill has an appropriate gap size to produce the uniform particle size.

11. A method of claim 10, wherein the gap size is in the range from 0.104 millimeters to 0.728 millimeters.

12. A method of claim 10, wherein the gap size is in the range from 0.2 to 0.3 millimeters and wherein the grain comprises corn kernels.

13. A method of claim 1, wherein the mechanically separating the stillage stream comprises centrifugation.

14. A method of claim 13, wherein the centrifugation comprises use of a disk type centrifuge.

15. A method of claim 1, wherein light phase material comprises an emulsion of water, oil/lipid, and solid materials.

16. A method of claim 2, wherein the recovery of essentially lipid material from the light phase material comprises chemical treatment prior to the separation in order to facilitate separation of an oil or lipid product from the light phase mixture.

17. A method of claim 4, wherein the aqueous phase material is mechanically processed to create a clarified aqueous phase mixture.

18. A method of claim 17, wherein mechanically processing the aqueous phase material comprises using a filter.

19. A method of claim 1, wherein the primary product(s) comprise alcohol.

* * * * *